US008597959B2

(12) United States Patent
Jing et al.

(10) Patent No.: US 8,597,959 B2
(45) Date of Patent: Dec. 3, 2013

(54) METHODS OF USE OF SOLID SUPPORT MATERIAL FOR BINDING BIOMOLECULES

(75) Inventors: Naiyong Jing, Woodbury, MN (US); William J. Schultz, North Oaks, MN (US); Chunmei Guo, Woodbury, MN (US); Michelle L. Legatt, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 848 days.

(21) Appl. No.: 12/595,862

(22) PCT Filed: Apr. 17, 2008

(86) PCT No.: PCT/US2008/060575
§ 371 (c)(1),
(2), (4) Date: Mar. 24, 2010

(87) PCT Pub. No.: WO2008/131063
PCT Pub. Date: Oct. 30, 2008

(65) Prior Publication Data
US 2010/0184103 A1    Jul. 22, 2010

Related U.S. Application Data

(60) Provisional application No. 60/912,699, filed on Apr. 19, 2007, provisional application No. 60/912,703, filed on Apr. 19, 2007, provisional application No. 60/912,707, filed on Apr. 19, 2007.

(51) Int. Cl.
*G01N 33/543* (2006.01)
*G01N 33/551* (2006.01)
*C12Q 1/00* (2006.01)

(52) U.S. Cl.
USPC .............. 436/518; 436/524; 436/532; 435/4

(58) Field of Classification Search
None
See application file for complete search history.

(56) References Cited

U.S. PATENT DOCUMENTS

| 2,801,185 | A | 7/1957 | Iler | |
|---|---|---|---|---|
| 3,337,351 | A | 8/1967 | Morehouse | 106/13 |
| 3,507,897 | A | 4/1970 | Kanner et al. | 260/448 |
| 3,976,497 | A | 8/1976 | Clark | 106/287 |
| 4,152,165 | A | 5/1979 | Langager et al. | 106/2 |
| 4,338,377 | A | 7/1982 | Beck et al. | 428/428 |
| 4,522,958 | A | 6/1985 | Das et al. | 423/212 |
| 5,002,884 | A | 3/1991 | Kobayashi et al. | 435/176 |
| 5,126,394 | A | 6/1992 | Revis et al. | 524/548 |
| 5,137,765 | A | 8/1992 | Farnsworth | 428/64 |
| 5,648,407 | A | 7/1997 | Goetz et al. | 523/213 |
| 5,723,175 | A | 3/1998 | Scholz et al. | 427/161 |
| 5,873,931 | A | 2/1999 | Scholz et al. | 106/13 |
| 5,888,594 | A | 3/1999 | David et al. | 427/577 |
| 5,948,166 | A | 9/1999 | David et al. | 118/718 |
| 5,997,621 | A | 12/1999 | Scholz et al. | 106/13 |
| 6,040,053 | A | 3/2000 | Scholz et al. | 428/412 |
| 6,191,214 | B1 | 2/2001 | Cheng et al. | 524/591 |
| 6,319,674 | B1 | 11/2001 | Fulcrand et al. | 435/7.1 |
| 6,467,897 | B1 | 10/2002 | Wu et al. | 347/102 |
| 6,727,309 | B1 | 4/2004 | Paiva et al. | 524/438 |
| 6,767,410 | B2 | 7/2004 | Aubay et al. | 134/42 |
| 6,783,947 | B1 | 8/2004 | de Keezer et al. | 435/7.93 |
| 6,979,446 | B2 | 12/2005 | Patti et al. | 424/165 |
| 6,998,042 | B2 | 2/2006 | Wormsbecher | 210/198 |
| 7,022,416 | B2 | 4/2006 | Teranishi | 428/601 |
| 7,045,146 | B2 | 5/2006 | Caruso et al. | 424/463 |
| 7,074,463 | B2 | 7/2006 | Jones et al. | 428/1.1 |
| 7,094,747 | B2 | 8/2006 | Geffroy et al. | 510/476 |
| 7,115,688 | B1 | 10/2006 | Mirkin et al. | 526/127 |
| 7,179,513 | B2 | 2/2007 | Jones et al. | 428/1.5 |
| 7,189,768 | B2 | 3/2007 | Baran, Jr. et al. | 523/200 |
| 7,326,448 | B2 | 2/2008 | Jones et al. | 428/1.1 |
| 7,332,327 | B2 | 2/2008 | Vikholm et al. | 435/287.2 |
| 7,459,146 | B2 | 12/2008 | Baran, Jr. et al. | 424/46 |
| 7,488,807 | B2 | 2/2009 | Mach et al. | 530/388 |
| 2002/0150759 | A1 | 10/2002 | Jones et al. | 428/403 |
| 2003/0059954 | A1 | 3/2003 | Vikholm et al. | 436/518 |
| 2003/0092029 | A1 | 5/2003 | Josephson et al. | 435/6 |
| 2003/0143598 | A1 | 7/2003 | Garimella et al. | 435/6 |
| 2004/0039201 | A1 | 2/2004 | Lugade et al. | 544/213 |
| 2004/0058457 | A1 | 3/2004 | Huang et al. | 436/524 |
| 2004/0067503 | A1 | 4/2004 | Tan et al. | 435/6 |
| 2004/0115345 | A1 | 6/2004 | Huang et al. | 427/212 |
| 2004/0241101 | A1 | 12/2004 | Baran, Jr. et al. | 424/46 |
| 2004/0265392 | A1 | 12/2004 | Tovar et al. | 424/492 |

(Continued)

FOREIGN PATENT DOCUMENTS

| EP | 1 650 565 | 4/2006 |
|---|---|---|
| JP | 59-15473 | 1/1984 |

(Continued)

OTHER PUBLICATIONS

Delamarche, E., et al. Immobilization of antibodies on a photoactive self-assembled monolayer on gold. Langmuir, vol. 12, pp. 1997-2006, 1996.*

American Type Culture Collection, "ATTC No. 6538" Organism: *Staphylococcus aureus* subsp. *aureus* Rosenbach; Designations: FDA 209 [CIP 4.83; DSM 799; IFO 13276; NCIB 9518; NCTC 10788]; Manassas, VA, Available online [retrieved on Apr. 23, 2007] Retrieved from the internet: http://www.atcc.org/common/catalog/numSearch/numResults.cfm; (4 pgs.).

Bayer, E. et al.; "Application of avidin-biotin technology to affinity-based separations"; Journal of Chromatography; 510; (1990) pp. 3-11.

(Continued)

Primary Examiner — Rodney P. Swartz

(57) ABSTRACT

Functionalized solid support material with biomolecule-binding groups and uses thereof, wherein the biomolecule-binding groups include a plurality of aromatic groups, an amine group which bonds to a biomolecule through an aldehyde group, a hydrazine group which bonds to a biomolecule through an aldehyde group, or an alpha,beta-ethylenically or acetylenically unsaturated group with an electron withdrawing group.

15 Claims, No Drawings

(56) References Cited

U.S. PATENT DOCUMENTS

| | | | |
|---|---|---|---|
| 2005/0059068 A1 | 3/2005 | Huang et al. | 435/6 |
| 2005/0074551 A1 | 4/2005 | Huang et al. | 427/212 |
| 2005/0142563 A1 | 6/2005 | Haddad et al. | 435/6 |
| 2005/0200278 A1 | 9/2005 | Jones et al. | 313/582 |
| 2006/0134595 A1 | 6/2006 | Rapp et al. | 435/2 |
| 2006/0147674 A1 | 7/2006 | Walker, Jr. et al. | 428/141 |
| 2006/0147703 A1 | 7/2006 | Walker, Jr. et al. | 428/328 |
| 2006/0148104 A1 | 7/2006 | Marini et al. | 436/524 |
| 2006/0165998 A1 | 7/2006 | Jones et al. | |
| 2006/0194145 A1 | 8/2006 | Irvine et al. | 430/270 |
| 2006/0204676 A1 | 9/2006 | Jones et al. | 428/1.1 |
| 2006/0204679 A1 | 9/2006 | Jones et al. | 428/1.3 |
| 2006/0210726 A1 | 9/2006 | Jones et al. | 428/1.1 |
| 2007/0275042 A1 | 11/2007 | Anderson et al. | 424/445 |
| 2010/0047252 A1 | 2/2010 | Mach | 424/150 |
| 2010/0184103 A1 | 7/2010 | Jing et al. | 435/7.32 |
| 2010/0209946 A1 | 8/2010 | Jing et al. | 435/7.33 |

FOREIGN PATENT DOCUMENTS

| | | |
|---|---|---|
| WO | WO 01/12846 | 2/2001 |
| WO | WO 01/66820 | 9/2001 |
| WO | WO 2004/012855 | 2/2004 |
| WO | WO 2004/013605 | 2/2004 |
| WO | WO 2004/017042 | 2/2004 |
| WO | WO 2004/108902 | 12/2004 |
| WO | WO 2005/056827 | 6/2005 |
| WO | WO2006/083269 | 8/2006 |
| WO | WO 2007/021731 | 2/2007 |
| WO | WO 2008/131063 | 10/2008 |
| WO | WO 2008/140580 | 11/2008 |
| WO | WO 2009/009188 | 1/2009 |

OTHER PUBLICATIONS

David, M. et al.; "Plasma Deposition and Etching of Diamond-Like Carbon Films", AIchE Journal; vol. 37, No. 3; Mar. 1991; pp. 367-376.

Delamarche, E. et al.; "Immobilization of Antibodies on a Photoactive Self-Assembled Monolayer on Gold"; Langmuir; vol. 12, No. 8; (1996) pp. 1997-2006.

Friedrich et al;. "Determination of Plateau Moduli and Entanglement Molecular Weights of Polypropylenes of Different Taciticity"; Progess and Trends in Rheology V—Proceedings of the Fifth European Rheology Conference; Portoroz, Slovenia, Sep. 6-11, 1998 ; Abstract #387.

Fuentes, M. et al.; "Preparation of inert magnetic nano-particles for the directed immobilization of antibodies"; Biosensors and Bioelectronics; 20 (2005) pp. 1380-137.

Green, N.M.; "Avidin, 3. The Nature of the Biotin-Binding Site"; Biochem. J.; vol. 89; (1963) pp. 599-609.

Green, M. "Avidin"; Advances in Protein Chemistry; vol. 29; Academic Press: New York; (1975); Title page publishers page and pp. 85-133.

MacBeath, G. et al.; "Printing Small Molecules as Microarrays and Detecting Protein-Ligand Interactions en Masse"; J. Am. Chem. Soc.; vol. 121, No. 34; (1999) pp. 7967-7968.

Metzke, M. et al.; "A Novel Carbohydrate-Derived Side-Chain Polyether with Excellent Protein Resistance"; J. Am. Chem. Soc.; vol. 125, No. 6; (2003) pp. 7760-7761.

Phenyl Sepharose CL-4B product datasheet. GE Healthcare Bio-Sciences Corporation: Piscataway, NJ. Available Online [retrieved Apr. 23, 2007]. Retrieved from the Internet: http://www6.gelifesciences.com/aptrix/upp00919.nsf/Content/22721E84D2DC7DFEC1256F5E000DBE6B/$file/71708000AE.pdt; (12 pgs.).

Wang, R. et al.; "Light-induced amphiphilic surfaces"; Nature; vol. 388; (1997) pp. 431-432.

Wei, R.D. et al.; "Dissociation of Avidin-Biotin Complex in vivo"; Experientia; vol. 27; (1971); pp. 366-368.

Yoon, T.J. et al; "Specific Targeting, Cell Sorting, and Bioimaging with Smart Magnetic Silica Core-Shell Nanomaterials"; Small; vol. 2; No. 2; (2006) pp. 209-215.

Zheng, M. et al.; "Nanoparticles Comprising A Mixed Monolayer for Specific Bindings with Biomolecules" J. Am. Chem. Soc.; vol. 126, No. 38; (2004) pp. 12047-12054.

U.S. Appl. No. 60/912,703, filed Apr. 19, 2007 and entitled "Methods of Use of Solid Support Material Having Alpha,Beta-Unsaturated Groups".

U.S. Appl. No. 60/912,707, filed Apr. 19, 2007 and entitled "Solid Support Material Having Amine and/or Hydrazine Functional Groups and Uses Therof for Attaching Biomolecules".

Ho, K. et al.; "Using Biofunctionalized Nanoparticles To Probe Pathogenic Bacteria"; Analytical Chemistry, vol. 76, No. 24, Dec. 15, 2004; pp. 7162-7168.

NIH News Release dated Thursday May 27, 1999; pp. 1-3 retrieved from http://www.nih.gov/news/pr/may99/niaid-27.htm on Jun. 1, 2011 entitled "Experimental Staph Vaccine Broadly Protective in Animal Studies".

Zhang, K. et al.; "Monodisperse Silica-Polymer Core-Shell Microspheres via Surface Grafting and Emulsion Polymerization"; Macromolecular Materials and Engineering, vol. 288, No. 4, 2003; pp. 380-385.

Zhang, J. et al.; "Modification of Nano-alumina Surface by Michael Addition Reaction"; Chinese Chemical Letters; vol. 17, No. 2; 2006; pp. 251-252.

Kim, S. et al.; "Oragnically Modified Silica Nanoparticles Co-encapsulating Photosensitizing Drug and Aggregation-Enhanced Two-Photon Absorbing Fluorescent Dye Aggregates for Two-Photon Photodynamic Therapy"; J. Am. Chem. Soc., vol. 129, No. 9; 2007; pp. 2669-2675.

* cited by examiner

METHODS OF USE OF SOLID SUPPORT MATERIAL FOR BINDING BIOMOLECULES

CROSS REFERENCE TO RELATED APPLICATIONS

This application is a national stage filing under 35 U.S.C. 371 of PCT/US2008/060575, filed Apr. 17, 2008, which claims the benefit of U.S. Provisional Patent Application Nos. 60/912,699, 60/912,703, and 60/912,707; each filed on Apr. 19, 2007, each incorporated herein by reference in its entirety.

BACKGROUND

Early, sensitive detection of clinical conditions, such as an infection or precancerous changes in living tissue, have significant beneficial effects for diagnosis and treatment of diseases. Factors that affect the detection of clinical conditions include materials and methods used to capture, concentrate, and/or purify biomolecules that are associated with the clinical condition. Additional factors affecting detection and diagnosis include means for detecting extremely small amounts, such as picogram quantities, of the biomolecules of interest.

Current techniques for the detection of clinical conditions are generally time consuming and involve considerable manipulation to obtain a suitable sample. The techniques also are subject to a number of interfering substances in biological samples that can render the test result invalid. Thus, there is a need to provide materials and processes to capture and purify biomolecules from such inhibitory substances.

The sensitivity and specificity of current techniques for the detection of clinical conditions is affected by the capture of nonspecific substances, which typically hinder the detection of small quantities of biomolecules. Thus, there is a need for materials and methods to reduce the capture of nonspecific substances when concentrating and detecting the presence of biomolecules of interest.

SUMMARY

The invention relates to the use of a solid support material having a functionalized surface for attaching biomolecules, preferably for the capture of a target biological analyte.

In one embodiment, the present invention provides a method of capturing a target biological analyte. The method involves: providing a solid support material having a surface that includes optional shielding groups covalently bonded to the surface (preferably through nonreversible covalent bonds), and biomolecule-binding groups disposed on the surface (preferably, the biomolecule-binding groups are covalently bonded to the surface, and more preferably, they are bonded through nonreversible covalent bonds), wherein the biomolecule-binding groups include one or more aromatic groups (preferably a plurality of aromatic groups). The solid support material is then contacted with a polypeptide under conditions effective to attach (preferably through a noncovalent hydrophobic interaction) the polypeptide to one or more of the aromatic groups. The polypeptide can be a capture agent for a target biological analyte. Such polypeptide capture agents can be used in methods that involve contacting the surface with the polypeptide capture agent attached thereto having a sample suspected of containing a target biological analyte.

In certain methods, the shielding groups are present (i.e., they are not optional). In certain methods, particularly when the shielding groups are optional, the methods preferably include the proviso that the polypeptide capture agent and/or target biological analyte are not eluted from the solid support material. Alternatively, or additionally, for certain embodiments, particularly when the shielding groups are optional, the biomolecule-binding groups are disposed on at least 25% of the area of the surface of the solid support material.

For certain embodiments, the polypeptide capture agent is an antibody. For certain embodiments, the solid support material includes a plurality of antibodies of different specificities. For certain embodiments, the target biological analyte is a microbe, such as a bacterium (e.g., *Staphylococcus aureus*). For certain preferred embodiments, the antibody is attached to one or more of the aromatic group(s) through the Fc region of the antibody.

For certain embodiments, the shielding groups include poly(alkylene oxide)-containing groups, preferably poly(ethylene oxide)-containing groups. The shielding groups are monovalent and covalently bonded (preferably, through nonreversible covalent bonds) to the surface. For certain embodiments, the shielding groups include poly(alkylene oxide)-containing groups, ethylene glycol ether-containing groups, poly(ethylene oxide) ether-containing groups, ethylene glycol lactate-containing groups, sugar-containing groups, polyol-containing groups, crown ether-containing groups, oligo glycidyl ether-containing groups (including methyl ether or hydroxyethyl ether), hydroxyl acrylamide-containing groups, organosulfonate-containing groups, organocarboxylate groups, or combinations thereof.

For certain embodiments, the solid support material includes a film, sheet, membrane, filter, fiber, foam, bead, particle, bottle, plate, tube, rod, pipe, wafer, or combination thereof. For certain embodiments, the solid support material includes a microtiter plate or other assay vessel. For certain embodiments, the solid support material includes particulate material, which can include nanoparticles.

For certain embodiments, the solid support material further includes hydrophilic groups covalently bonded to the surface (preferably through nonreversible covalent bonds). For certain embodiments, the solid support material includes nanoparticles and the hydrophilic groups assist in dispersion of the nanoparticles in an aqueous biological environment (and, hence, are referred to as water-dispersible groups). For certain embodiments, the shielding groups and the hydrophilic groups (e.g., water-dispersible groups) are the same, whereas in other embodiments the hydrophilic groups (e.g., water-dispersible groups) are distinct from the shielding groups. Preferably, the hydrophilic groups (e.g., water-dispersible groups) include carboxylic acid groups, sulfonic acid groups, phosphonic acid groups, salts thereof, or combinations thereof.

The biomolecule-binding groups include one or more aromatic groups (preferably a plurality of aromatic groups). For certain embodiments, the biomolecule-binding groups include diphenyl groups, triphenyl groups, or a combination thereof. For certain embodiments, the biomolecule-binding groups include diphenyl groups.

For certain embodiments, the solid support material further includes reporter groups attached to the surface (preferably through covalent bonds, and more preferably through nonreversible covalent bonds). For certain embodiments, the reporter groups include fluorescent groups.

In one embodiment, the present invention provides a method of preparing a solid support material having a biomolecule attached thereto. The method involves: providing a solid support material having a surface; optionally providing a shielding compound having a shielding group and a surface-bonding group; providing a biomolecule-binding compound comprising one or more aromatic groups (preferably a plurality of aromatic groups); optionally covalently bonding (preferably through a nonreversible covalent interaction) the shielding group to the surface of the solid support material through the surface-bonding group, and disposing the biomolecule-binding compound on the surface of the solid support material (preferably the biomolecule-binding compound is bonded to the surface through covalent bonding, that is preferably nonreversible); and contacting the solid support material with a polypeptide under conditions effective to attach the polypeptide to one or more (preferably two or more) of the aromatic group(s). For certain embodiments, the polypeptide is a capture agent (e.g., an antibody) for a target biological analyte, whereas for other embodiments, the polypeptide is the target biological analyte.

In certain methods, the shielding groups are present (i.e., they are not optional). In certain methods, particularly when the shielding groups are optional, the methods preferably include the proviso that the polypeptide is not subsequently eluted from the solid support material. Alternatively, or additionally, for certain embodiments, particularly when the shielding groups are optional, the biomolecule-binding groups are disposed on at least 25% of the area of the surface of the solid support material.

The methods can further include: providing a reporter molecule comprising a reporter group (e.g., fluorescent group) and a surface-bonding group; and attaching (preferably covalently bonding) the reporter group to the surface of the solid support material through the surface-bonding group (preferably through nonreversible covalent bonds). For certain embodiments, the shielding compound is covalently bonded to the surface of the solid support material prior to the reporter molecule being bonded thereto.

The present invention also provides a solid support material prepared by the methods described herein. In one embodiment, the solid support material has a surface that includes: biomolecule-binding groups including a one or more (preferably a plurality of) aromatic groups disposed on the surface (preferably, covalently bonded to the surface); shielding groups covalently bonded to the surface; and a polypeptide (preferably an antibody) attached to one or more of the aromatic group(s) through a noncovalent hydrophobic interaction. In another embodiment, the solid support material has a surface that includes: biomolecule-binding groups disposed on at least 25% of the area of the surface (preferably, covalently bonded to the surface); wherein the biomolecule-binding groups comprise one or more (preferably a plurality of) aromatic groups; optional shielding groups covalently bonded to the surface; and a polypeptide (preferably an antibody) attached to one or more of the aromatic groups through a noncovalent hydrophobic interaction.

In certain embodiments, the polypeptide is an antibody and is attached to one or more aromatic groups through the Fc region of the antibody. Preferably, the polypeptide is an antibody and is attached to two or more of a plurality of aromatic groups through the Fc region of the antibody. The attachment of the Fc region to the binding group is preferred because in such an orientation, the biological activities of the antibodies remain substantially unchanged.

In one embodiment, the present invention provides a method of capturing a target biological analyte. The method involves: providing a solid support material having a surface that includes optional shielding groups covalently bonded to the surface (preferably through nonreversible covalent bonds), and biomolecule-binding groups bonded to the surface through covalent bonds (preferably through nonreversible covalent bonds), wherein the biomolecule-binding groups include nontertiary amine groups and/or hydrazine groups. The solid support material is then contacted with an aldehyde-functional biomolecule under conditions effective to covalently bond the biomolecule to one or more biomolecule-binding groups to form an —Ar—N=C(H)— and/or —Ar—NHN=C(H)— linkage, wherein Ar is an aryl group. The biomolecule is a capture agent for a target biological analyte, and the method involves contacting the surface with the biomolecule capture agent covalently bonded thereto with a sample suspected of containing a target biological analyte.

For certain embodiments, the biomolecule capture agent is an antibody, wherein the solid support material includes a plurality of antibodies of different specificities. For certain embodiments, the target biological analyte is a microbe, such as a bacterium (e.g., *Staphylococcus aureus*).

For certain embodiments, the shielding groups are present and include poly(alkylene oxide)-containing groups, preferably poly(ethylene oxide)-containing groups. The shielding groups are monovalent and covalently bonded (preferably, through nonreversible covalent bonds) to the surface. For certain embodiments, the shielding groups comprise poly(alkylene oxide)-containing groups, ethylene glycol ether-containing groups, poly(ethylene oxide) ether-containing groups, ethylene glycol lactate-containing groups, sugar-containing groups, polyol-containing groups, crown ether-containing groups, oligo glycidyl-containing groups, hydroxyl acrylamide-containing groups, organosulfonate-containing groups, organocarboxylate-containing groups, or combinations thereof.

For certain embodiments, the solid support material includes a film, sheet, membrane, filter, fiber, foam, bead, particle, bottle, plate, tube, rod, pipe, wafer, or combination thereof. For certain embodiments, the solid support material includes a microtiter plate or other assay vessel. For certain embodiments, the solid support material includes particulate material, which can include nanoparticles.

For certain embodiments, the solid support material further includes hydrophilic groups covalently bonded to the surface (preferably through nonreversible covalent bonds). For certain embodiments, the solid support material includes nanoparticles and the hydrophilic groups assist in dispersion of the nanoparticles in an aqueous biological environment (and, hence, are referred to as water-dispersible groups). For certain embodiments, the shielding groups and the hydrophilic groups (e.g., water-dispersible groups) are the same, whereas in other embodiments the hydrophilic groups (e.g., water-dispersible groups) are distinct from the shielding groups. Preferably, the hydrophilic groups (e.g., water-dispersible groups) include carboxylic acid groups, sulfonic acid groups, phosphonic acid groups, salts thereof, or combinations thereof.

The biomolecule-binding groups include nontertiarty amine groups and/or hydrazine groups. For certain embodiments, the biomolecule-binding groups include nontertiarty amine groups. For certain embodiments, the nontertiary amine groups are primary amine groups.

For certain embodiments, the solid support material further includes reporter groups attached to the surface (preferably through covalent bonds, and more preferably through nonreversible covalent bonds). For certain embodiments, the reporter groups include fluorescent groups.

In one embodiment, the present invention provides a method of preparing a solid support material having a biomolecule attached thereto. The method involves: providing a solid support material having a surface; providing a biomolecule-binding compound having a nontertiary amine group and/or a hydrazine group and a surface-bonding group; optionally providing a shielding compound having a shielding group and a surface-bonding group; covalently bonding the biomolecule-binding group and optional shielding group to the surface of the solid support material through the surface-bonding groups; wherein, preferably, the biomolecule-binding group (and preferably the shielding group) is bonded to the surface through a nonreversible covalent bond; and contacting the solid support material with an aldehyde-functional biomolecule under conditions effective to covalently bond the biomolecule to a biomolecule-binding group to form an —Ar—N=C(H)— and/or —Ar—NHN=C(H)— linkage, wherein Ar is an aryl group. For certain embodiments, the biomolecule is a capture agent (e.g., an antibody) for a target biological analyte, whereas for other embodiments, the biomolecule is the target biological analyte.

The method can further include: providing a reporter molecule comprising a reporter group (e.g., fluorescent group) and a surface-bonding group; and attaching (preferably covalently bonding) the reporter group to the surface of the solid support material through the surface-bonding group (preferably through nonreversible covalent bonds). For certain embodiments, the shielding compound is covalently bonded to the surface of the solid support material prior to the reporter molecule being bonded thereto.

The present invention also provides a solid support material formed by the methods presented herein. In one embodiment, a solid support material is provided wherein the surface of the material includes: biomolecule-binding groups bonded to the surface through nonreversible covalent bonds; an aldehyde-functional biomolecule (preferably an oxidized antibody) covalently bonded to one or more biomolecule-binding groups through an —Ar—N=C(H)— and/or —Ar—NHN=C(H)— linkage, wherein Ar is an aryl group; and shielding groups covalently bonded to the surface.

In one embodiment, the present invention provides a method of capturing a target biological analyte. The method involves: providing a solid support material having a surface that includes shielding groups covalently bonded to the surface (preferably through nonreversible covalent bonds), and biomolecule-binding groups bonded to the surface through covalent bonds (preferably through nonreversible covalent bonds), wherein the biomolecule-binding groups include alpha,beta-ethylenically or acetylenically unsaturated groups and electron withdrawing groups. The solid support material is then contacted with an amino-functional biomolecule under conditions effective to covalently bond the biomolecule to one or more biomolecule-binding groups through a carbon-nitrogen bond between the amino group of the biomolecule and the beta position of the alpha,beta-ethylenically or acetylenically unsaturated group. In this method, the biomolecule is a capture agent for a target biological analyte, and the method involves contacting the surface with the biomolecule capture agent covalently bonded thereto with a sample suspected of containing a target biological analyte.

For certain embodiments, the biomolecule capture agent is an antibody, wherein the solid support material includes a plurality of antibodies of different specificities. For certain embodiments, the target biological analyte is a microbe, such as a bacterium (e.g., *Staphylococcus aureus*).

For certain embodiments, the shielding groups include poly(alkylene oxide)-containing groups, preferably poly(ethylene oxide)-containing groups. The shielding groups are monovalent and covalently bonded (preferably, through nonreversible covalent bonds) to the surface. For certain embodiments, the shielding groups include poly(alkylene oxide)-containing groups, ethylene glycol ether-containing groups, poly(ethylene oxide) ether-containing groups, ethylene glycol lactate-containing groups, sugar-containing groups, polyol-containing groups, crown ether-containing groups, oligo glycidyl-containing groups, hydroxyl acrylamide-containing groups, organosulfonate-containing groups, organocarboxylate-containing groups, or combinations thereof.

For certain embodiments, the solid support material includes a film, sheet, membrane, filter, fiber, foam, bead, particle, bottle, plate, tube, rod, pipe, wafer, or combination thereof. For certain embodiments, the solid support material includes a microtiter plate or other assay vessel. For certain embodiments, the solid support material includes particulate material, which can include nanoparticles.

For certain embodiments, the solid support material further includes hydrophilic groups covalently bonded to the surface (preferably through nonreversible covalent bonds). For certain embodiments, the solid support material includes nanoparticles and the hydrophilic groups assist in dispersion of the nanoparticles in an aqueous biological environment (and, hence, are referred to as water-dispersible groups). For certain embodiments, the shielding groups and the hydrophilic groups (e.g., water-dispersible groups) are the same, whereas in other embodiments the hydrophilic groups (e.g., water-dispersible groups) are distinct from the shielding groups. Preferably, the hydrophilic groups (e.g., water-dispersible groups) include carboxylic acid groups, sulfonic acid groups, phosphonic acid groups, salts thereof, or combinations thereof.

The biomolecule-binding groups include an alpha,beta-ethylenically or acetylenically unsaturated group with an electron withdrawing group at the alpha position. For certain embodiments, the electron withdrawing groups include carbonyls, ketones, esters, amides, —SO$_2$—, —SO—, —CO—CO—, —CO—COOR, sulfonamides, halides, trifluoromethyl, sulfonamides, halides, maleimides, maleates, or combinations thereof. For certain embodiments, the biomolecule-binding groups are acrylates or alpha,beta-unsaturated ketones. For certain embodiments, the biomolecule-binding groups are multifunctional acrylates.

For certain embodiments, the solid support material further includes reporter groups attached to the surface (preferably through covalent bonds, and more preferably through nonreversible covalent bonds). For certain embodiments, the reporter groups include fluorescent groups.

In a particularly preferred embodiment, the present invention provides a method of capturing a target biological analyte that includes: providing nanoparticles (preferably silica nanoparticles) having a surface that includes: organocarboxylate-containing and/or organosulfonate-containing shielding groups covalently bonded to the surface; and biomolecule-binding groups covalently bonded to the surface, wherein the biomolecule-binding groups include acrylate groups; contacting the solid support material with an amino-functional biomolecule under conditions effective to covalently bond the biomolecule to one or more biomolecule-binding groups through a carbon-nitrogen bond between the amino group of the biomolecule and the beta position of the acrylate group; wherein the biomolecule is a capture agent for a target biological analyte; and contacting the surface with the biomolecule capture agent covalently bonded thereto with a sample suspected of containing a target biological analyte. In this embodiment, preferably there are no poly(alkylene oxide) groups present on the nanoparticles as shielding or water-dispersible groups.

In one embodiment, the present invention provides a method of preparing a solid support material having a biomolecule attached thereto. The method involves: providing a solid support material having a surface; providing a shielding compound having a shielding group and a surface-bonding group; providing a biomolecule-binding compound having an alpha,beta-ethylenically unsaturated group, an electron withdrawing group, and a surface-bonding group; covalently bonding the shielding group and biomolecule-binding group to the surface of the solid support material through the surface-bonding groups; wherein the biomolecule-binding group and shielding group are bonded to the surface through nonreversible covalent bonds; and contacting the solid support material with an amino-functional biomolecule under conditions effective to covalently bond the biomolecule to one or more biomolecule-binding groups through a carbon-nitrogen bond between the amino group of the biomolecule and the beta position of the alpha,beta-ethylenically unsaturated group. For certain embodiments, the biomolecule is a capture agent (e.g., an antibody) for a target biological analyte, whereas for other embodiments, the biomolecule is the target biological analyte.

The method can further include: providing a reporter molecule including a reporter group (e.g., fluorescent group) and a surface-bonding group; and attaching (preferably covalently bonding) the reporter group to the surface of the solid support material through the surface-bonding group (preferably through nonreversible covalent bonds). For certain embodiments, the shielding compound is covalently bonded to the surface of the solid support material prior to the reporter molecule being bonded thereto.

In a particularly preferred embodiment, the present invention provides a method of preparing a solid support material having a biomolecule attached thereto that includes: providing nanoparticles (preferably silica nanoparticles), each having a surface; providing a shielding compound that includes an organocarboxylate-containing and/or organosulfonate-containing group and a surface-bonding group; providing a biomolecule-binding compound including an acrylate group and a surface-bonding group; covalently bonding the organocarboxylate and/or organosulfonate group and acrylate group to the surface of the nanoparticles through the surface-bonding groups; and contacting the nanoparticles with an amino-functional biomolecule under conditions effective to covalently bond the biomolecule to one or more acrylate groups through a carbon-nitrogen bond between the amino group of the biomolecule and the beta position of the acrylate group. In this embodiment, preferably there are no poly(alkylene oxide) groups present on the nanoparticles as shielding or water-dispersible groups.

DEFINITIONS

"Biomolecule-binding groups" are functional groups that are reactive with biomolecules, thereby forming covalent bonds, preferably nonreversible covalent bonds. Biomolecule-binding groups may include one or more aromatic groups that are capable of interacting with polypeptides. It is believed that the interaction between a biomolecule and a biomolecule-binding group including one or more aromatic groups may be through a noncovalent hydrophobic interaction.

"Nonreversible covalent bond" in the context of the present invention means a covalent bond that is nonreversible under physiologic conditions. A nonreversible covalent bond does not include a bond that is in equilibrium under physiologic conditions, such as a gold-sulfur bond, that would allow the attached groups to migrate from one solid support (e.g., particle) to another and/or that would allow any foreign species containing —SH or —S—S— to replace the desired substituents.

"Shielding groups" are monovalent groups that are capable of reducing, and preferably preventing, nonspecific binding of biomolecules other than the biomolecules of interest.

"Hydrophilic groups" (e.g., "water-dispersible groups") are monovalent groups that provide hydrophilicity to the surface of the solid support material. Preferably, if such groups are attached to nanoparticles, they are capable of reducing, and preferably preventing, excessive agglomeration and precipitation of nanoparticles in an aqueous biological environment, and are referred to as "water-dispersible groups." Certain of the hydrophilic groups may also function as shielding groups (e.g., poly(ethylene oxide)-containing groups) for nonspecific binding.

"Nanoparticles" are herein defined as nanometer-sized particles, preferably with an average particle size of no greater than 200 nanometers (nm). As used herein, "particle size" and "particle diameter" have the same meaning and are used to refer to the largest dimension of a particle (or agglomerate thereof).

In this context, "agglomeration" refers to a weak association between particles which may be held together by charge or polarity and can be broken down into smaller entities.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a surface that comprises "a" biomolecule-binding group can be interpreted to mean that the surface includes "one or more" biomolecule-binding groups. Similarly, a method for capturing "a" target biological analyte can be interpreted to mean that the method can involve capturing "one or more" target biological analytes.

The term "and/or" means one or all of the listed elements or a combination of any two or more of the listed elements.

As used herein, the term "or" is generally employed in its sense including "and/or" unless the content clearly dictates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

The invention relates to the use of a functionalized surface of a solid support material. The functionalized solid support material of the present invention is useful in the design and fabrication of devices for which binding agents are needed for the attachment and immobilization of biomolecules. Preferably, the surface of the solid support material is designed to covalently attach biomolecules without perturbing their bio-orientation or bioactivity.

The surface of the solid support material of the present invention includes biomolecule-binding groups covalently bonded to the surface (preferably, through nonreversible covalent bonds). Such biomolecule-binding groups provide for the selective attachment of a biomolecule of interest (e.g., a target biological analyte) to the surface. Selective attachment may be achieved by a variety of techniques. For example, certain embodiments involve the covalent bonding of biomolecular capture agents (i.e., biomolecule capture agents), such as specific antibodies or proteins, to the surface, which can be used for specific bio-recognition of target biological analytes, such as bacteria.

The surface of the solid support material of the present invention also includes shielding groups covalently bonded to the surface (preferably through nonreversible covalent bonds). Shielding groups are used to reduce, and preferably prevent, the nonspecific binding of biomolecules other than the biomolecules of interest (e.g., biomolecule capture agents and/or target biological analytes). By reducing or preventing nonspecific binding, shielding groups contribute to enhanced sensitivity, accuracy, and reproducibility of bio-recognition assays, for example. Such shielding groups are monovalent and preferably nonreversibly covalently bonded (preferably nonreversibly) to the surface.

If desired, optional hydrophilic groups can be covalently bonded to the surface of the solid support material (preferably though nonreversible covalent bonds). In certain embodiments, the shielding groups and the hydrophilic groups can be the same. For example, poly(ethylene oxide)-containing groups can provide both shielding and hydrophilicity to the solid support material.

If desired, particularly if the solid support material includes nanoparticles, the hydrophilic groups provide dispersibility to the nanoparticles in an aqueous biological environment. In such embodiments, the hydrophilic groups are referred to as water-dispersible groups.

Generally, it is advisable to have high coverage of the reactive groups on the surface of the solid support material (e.g., silanol groups on the surface of silica) to reduce the tendency for nonspecific binding (and agglomeration if the solid support material is particulate material, such as nanoparticles). It is usually advisable that most of the reactive groups on the surface of the solid support material (i.e., surface functional groups) are reacted with biomolecule-binding groups and optional shielding and/or hydrophilic groups. As suitable solid support materials of this invention typically have very large number of accessible reactive sites, even a high percentage coverage by shielding groups and/or hydrophilic groups does not preclude the attachment of a usefully large number of biomolecule-binding groups. This is especially true for smaller sized nanoparticles, which have a large number of surface functional groups (i.e., surface reactive groups).

The reactive groups on the solid support materials (i.e., solid supports) are complementary groups capable of reacting with the surface-bonding group A (see below) in the compounds which bind to the surface (biomolecule-binding compounds of the formula A-L-B, shielding compounds of the formula A-L-Sh, hydrophilic (e.g., water-dispersible) compounds of the formula A-L-WD, and reporter compounds of the formula A-L-Rp, as discussed below). Any suitable combination of surface reactive groups (i.e., the reactive groups on the solid support material) and surface-bonding groups A may be used as long as the surface reactive groups are not reactive with the biomolecule-binding group B (of the biomolecule-binding compound), which is a functional group capable of interaction with a biomolecule (typically through covalent bonds).

In the above formulations, L represents an organic linker or a bond. Organic linkers L can be linear or branched alkylene, arylene, or a combination of alkylene and arylene groups, optionally including heteroatoms (including S, O, N, P, or mixtures thereof). Examples of L groups include ethylene oxide-containing oligomers or polymeric groups, ethylene-imine-containing oligomers or polymeric groups, and ethyl-enesulfide-containing oligmers or polymeric groups. Although the L groups can include divalent ethylene oxide-containing oligomers or polymeric groups, for example, which may also provide shielding and/or hydrophilic characteristics to the solid support material, the shielding groups and hydrophilic groups referred to herein are separate and distinct monovalent groups. By this it is meant that the shielding groups and hydrophilic groups are terminal groups and not a divalent linker for another group, particularly the biomolecule-binding group. Thus, if the biomolecule-binding group B is linked to the surface through a divalent ethylene oxide-containing oligomer, the solid support materials of the present invention preferably include separate and distinct shielding groups, which may include monovalent ethylene oxide-containing oligomers (i.e., groups without a reactive end group).

SOLID SUPPORT MATERIAL

The solid support material can have any useful form including, but not limited to, films, sheets, membranes, filters, nonwoven or woven fibers, foams, hollow or solid beads, particles (including nanoparticles), bottles, plates, tubes, rods, pipes, or wafers. The solid support can be porous or nonporous, rigid or flexible, transparent or opaque, clear or colored, and reflective or nonreflective. Suitable solid support materials include, for example, polymeric materials, glasses, silicons, ceramics, metals, metal oxides, hydrated metal oxides, or combinations thereof. The solid support material can be magnetic if desired. The solid support material can be in the form of a microtiter plate or other assay vessel.

The solid supports can have a single layer or multiple layers of material. For example, in some embodiments, the solid support can have one or more second layers that provide support for a first layer that includes a complementary group capable of reacting with the surface-bonding group A in the compounds which bind to the surface. The first layer is the outer layer of the solid support.

Suitable polymeric solid support materials include, but are not limited to, polyolefins, polystyrenes, polyacrylates, polymethacrylates, polyacrylonitriles, poly(vinylacetates), polyvinyl alcohols, polyvinyl chlorides, polyoxymethylenes, polycarbonates, polyamides, polyimides, polyurethanes, phenolics, polyamines, amino-epoxy resins, polyesters, silicones, cellulose based polymers, polysaccharides, or combinations thereof. In some embodiments, the polymeric material is a copolymer prepared using a comonomer having a complementary group capable of reacting with an A group. For example, the comonomer can contain a carboxy, mercapto, hydroxy, amino, or alkoxysilyl group. These groups are able to react with surface-bonding groups A, such as amino, carbon-carbon double bond, alkoxylsilanes, or chorosilanes.

Suitable glass and ceramic solid support materials can include, for example, sodium, silicon, aluminum, lead, boron, phosphorous, zirconium, magnesium, calcium, arsenic, gallium, titanium, copper, or combinations thereof. Glasses typically include various types of silicate-containing materials. The solid support can be a silicon-based material such as a dielectric material or a material suitable for use in integrated circuits or other electronic devices.

An organic polymeric substrate can be coated with an inorganic layer, such as a thin layer of $SiO_2$. Such materials can be created by the known methods, such as vapor deposition.

Alternatively, the solid support can include a layer of diamond-like glass as disclosed in International Patent Application WO 01/66820 A1. The diamond-like glass is an amorphous material that includes carbon, silicon, and one or more elements selected from hydrogen, oxygen, fluorine, sulfur, titanium, or copper. Some diamond-like glass materials are formed from a tetramethylsilane precursor using a plasma process. A hydrophobic material can be produced that is further treated in an oxygen plasma to control the silanol concentration on the surface.

Diamond-like glass can be in the form of a thin film or in the form of a coating on another layer or material in the solid support. In some applications, the diamond-like glass can be in the form of a thin film having at least 30 weight percent (wt-%), at least 25 wt-% silicon, and up to 45 wt-% oxygen. Such films can be flexible and transparent. In some embodiments, the diamond-like glass is the outer layer of a multilayer solid support. In a specific example, the second layer of the solid support is a polymeric material and the first layer is a thin film of diamond-like glass. The surface-bonding group A is attached to the surface of the diamond-like glass.

In some multilayer solid supports, the diamond-like glass is deposited on a layer of diamond-like carbon. For example, the second layer is a polymeric film having a layer of diamond-like carbon deposited on a surface. A layer of diamond-like glass is deposited over the diamond-like carbon layer. The diamond-like carbon can, in some embodiments, function as a tie layer or primer layer between a polymeric layer and a layer of diamond-like glass in a multilayer solid support. For example, the multilayer solid support can include a polyimide or polyester layer, a layer of diamond-like carbon deposited on the polyimide or polyester, and a layer of diamond-like glass deposited on the diamond-like carbon. In another example, the multilayer solid support includes a stack of the layers arranged in the following order: diamond-like glass, diamond-like carbon, polyimide or polyester, diamond-like carbon, and diamond-like glass.

Diamond-like carbon films can be prepared, for example, from acetylene in a plasma reactor. Other methods of preparing such films are described U.S. Pat. Nos. 5,888,594 and 5,948,166 as well as in the article M. David et al., *AIChE Journal*, 37(3), 367-376 (March 1991).

Suitable metals, metal oxides, or hydrated metal oxides for solid supports can include, for example, gold, silver, platinum, palladium, aluminum, copper, chromium, iron, cobalt, nickel, zinc, and the like. Herein, silicon, and other metalloids, are also included within the scope of the term "metal." The metal-containing material can include alloys such as stainless steel, indium tin oxide, and the like.

In some embodiments, a metal-containing material is the outer layer of a multilayer solid support. For example, the solid support can have a polymeric second layer and a metal containing first layer. In one more specific example, the second layer is a polymeric film and the first layer is a thin film of gold. In other examples, a multilayer solid support includes a polymeric film coated with a titanium-containing layer and then with a gold-containing layer. That is, the titanium layer can function as a tie layer or a primer layer for adhering the layer of gold to the polymeric film. The polymeric film in some examples can be a polyester or polyimide film.

In still other examples of a multilayer solid support that includes a metal-containing material, a silicon support layer can be covered with one or more metal-containing material. In a specific example, a silicon support layer can be covered with a layer of chromium and then with a layer of gold. The chromium layer can improve the adhesion of the gold layer to the silicon layer.

Suitable and preferred solid supports of the present invention include nanoparticles, i.e., nanometer-sized particles. The term "nanometer-sized" refers to particles that are characterized by an average particle size (or average particle diameter for spherical particles) of preferably no greater than 200 nm (prior to surface modification). More preferably the average particle size is no greater than 150 nanometers (prior to surface modification), even more preferably no greater than 120 nm (prior to surface modification), and even more preferably no greater than 100 nm (prior to surface modification). Preferably, prior to surface modification, the average particle size of the nanoparticles is at least 5 nm, and more preferably at least 10 nm.

Average particle size of the nanoparticles can be measured using transmission electron microscopy. In the practice of the present invention, particle size may be determined using any suitable technique. Preferably, particle size refers to the number average particle size and is measured using an instrument that uses transmission electron microscopy or scanning electron microscopy. Another method to measure particle size is dynamic light scattering that measures weight average particle size. One example of such an instrument found to be suitable is the N4 PLUS SUB-MICRON PARTICLE ANALYZER available from Beckman Coulter Inc. of Fullerton, Calif.

It is also preferable that the nanoparticles be relatively uniform in size. Uniformly sized nanoparticles generally provide more reproducible results. Uniform nanoparticles preferably have a particle size that varies by less than ±25%.

Herein, nanoparticles are preferably surface modified to be water-dispersible to reduce, and preferably prevent, excessive agglomeration and precipitation of the particles in an aqueous buffer solution used in biological environments. Nanoparticle aggregation can result in undesirable precipitation, gelation, or a dramatic increase in viscosity; however, small amounts of agglomeration can be tolerated when the nanoparticles are in an aqueous buffer solution as long as the average size of the agglomerates (i.e., agglomerated particles) is preferably no greater than 200 nm. Thus, the nanoparticles are preferably referred to herein as colloidal nanoparticles since they can be individual particles or small agglomerates thereof.

The nanoparticles preferably have a surface area of at least 10 $m^2$/gram, more preferably at least 20 $m^2$/gram, and even more preferably at least 25 $m^2$/gram. The nanoparticles preferably have a surface area of greater than 600 $m^2$/gram.

Nanoparticles of the present invention may be porous or nonporous. They can include essentially only one material (e.g., silica), or they can be composite nanoparticles such as core-shell nanoparticles. A core-shell nanoparticle can include a core of an oxide (e.g., iron oxide) or metal (e.g., gold or silver) of one type, or a polymeric material, and a shell of another type of metal or metal oxide deposited on the core.

The unmodified nanoparticles may be provided as a sol rather than as a powder. Preferred sols generally contain from 15 wt-% to 50 wt-% of colloidal particles dispersed in a fluid medium. Representative examples of suitable fluid media for the colloidal particles include water, aqueous alcohol solutions, lower aliphatic alcohols, ethylene glycol, N,N-dimethylacetamide, formamide, or combinations thereof. The preferred fluid medium is aqueous, e.g., water and optionally one or more alcohols. When the colloidal particles are dispersed in an aqueous fluid, the particles may be stabilized due to common electrical charges that develop on the surface of each particle. The common electrical charges tend to promote dispersion rather than agglomeration or aggregation, because the similarly charged particles repel one another.

Inorganic sols in aqueous media are well known in the art and available commercially. For example, silica sols in water or water-alcohol solutions are available commercially under such trade names as LUDOX (manufactured by E.I. DuPont de Nemours and Co., Inc., Wilmington, Del.), NYACOL (available from Nyacol Co., Ashland, Mass.) or NALCO (manufactured by Nalco Chemical Co., Oak Brook, Ill.). One useful silica sol is NALCO 2327 available as a silica sol with mean particle size of 20 nanometers, pH 9.5, and solid content 40 wt-%. Additional examples of suitable colloidal silicas are described in U.S. Pat. No. 5,126,394. Preferred nanoparticles are silica nanoparticles.

The sols used in the present invention generally may include counter cations, in order to counter the surface charge of the colloids. Depending upon pH and the kind of colloids being used, the surface charges on the colloids can be negative or positive. Thus, either cations or anions are used as counter ions. Examples of cations suitable for use as counter ions for negatively charged colloids include $Na^+$, $K^+$, $Li^+$, a quaternary ammonium cation such as $NR_4^+$, wherein each R may be any monovalent moiety, but is preferably H or lower alkyl, such as —$CH_3$, combinations of these, and the like.

A variety of methods are available for modifying the surfaces of solid support materials, depending on the functionality of the surface.

The surface of the solid support typically includes a group capable of reacting with a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group. That is, the solid support includes a group capable of reacting with the surface-bonding group A (i.e., the solid support includes a group complementary to the group A). Solid supports can include a support material treated to form an outer layer that includes a complementary group (i.e., surface reactive group). The solid support can be prepared from any solid phase material known to have groups capable of reacting with surface-bonding group A and is not limited to the following examples of suitable materials.

If desired, a solid support surface can be treated, for example, with a plasma (e.g., with oxygen ions) to provide a surface reactive toward a chosen surface-bonding group A, or to provide free radicals capable of grafting reactive molecules such as acrylic acids with amines for group A, or to create surface hydroxyl groups able to react with an isocyanate as group A.

A carboxy group can react with a solid support containing a metal or metal oxide, in particular, wherein the metal is copper, iron, nickel, or aluminum.

A carboxy group or a halocarbonyl group can react with a solid support having a hydroxy group to form a carbonyloxy-containing attachment group. Examples of solid support materials having hydroxy groups include, but are not limited to, polyvinyl alcohol, hydroxy substituted esters of polymethacrylates, hydroxy substituted esters of polyacrylates, corona-treated polyethylene, and a polyvinyl alcohol coating on a support material such as glass or polymeric film.

A carboxy group or a halocarbonyl group can also react with a solid support having a mercapto group to form a carbonylthio-containing attachment group. Examples of solid support materials having a mercapto group include, but are not limited to, mercapto substituted esters of polyacrylates, mercapto substituted esters of polymethacrylates, and glass treated with a mercaptoalkylsilane.

Additionally, a carboxy group or a halocarbonyl group can react with a primary aromatic amino group, a secondary aromatic amino group, or a secondary aliphatic amino group to form a carbonylimino-containing attachment group. Examples of solid support materials having aromatic primary or secondary amino groups include, but are not limited to, polyamines, amine substituted esters of polymethacrylate, amine substituted esters of polyacrylate, polyethylenimines, and glass treated with an aminoalkylsilane.

A halocarbonyloxy group can react with a solid support having a hydroxy group to form an oxycarbonyloxy-containing attachment group. Examples of solid support materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or a polymeric film.

A halocarbonyloxy group can also react with a solid support having a mercapto group to form an oxycarbonylthio-containing attachment group. Examples of solid support materials having a mercapto group include, but are not limited to, mercapto substituted esters of polymethacrylates, mercapto substituted esters of polyacrylates, and glass treated with a mercaptoalkylsilane.

A cyano group can react with a solid support having an azido group to form a tetrazinediyl-containing attachment group. Examples of solid supports having azido groups include, but are not limited to, a coating of poly(4-azidomethylstyrene) on a glass or polymeric support. Suitable polymeric support materials include polyesters, polyimides, and the like.

A hydroxy group can react with a solid support having isocyanate group to form an oxycarbonylimino-containing attachment group. Suitable solid supports having isocyanate groups include, but are not limited to, a coating of 2-isocyanatoethylmethacrylate polymer on a support material. Suitable support materials include glass and polymeric materials such as polyesters, polyimides, and the like.

A hydroxy group can react with a solid support having a carboxy, carbonyloxycarbonyl, or halocarbonyl to form a carbonyloxy-containing attachment group. Suitable solid supports include, but are not limited to, a coating of acrylic acid polymer or copolymer on a support material or a coating of a methacrylic acid polymer or copolymer on a support material. Suitable support materials include glass and polymeric materials such as polyesters, polyimides, and the like. Other suitable solid supports include copolymers of polyethylene with polyacrylic acid, polymethacrylic acid, or combinations thereof.

A mercapto group can react with a solid support having isocyanate groups. The reaction between a mercapto group and an isocyanate group forms a thiocarbonylimino-containing attachment group. Suitable solid supports having isocyanate groups include, but are not limited to, a coating of 2-isocyanatoethylmethacrylate polymer on a support material. Suitable support materials include glass and polymeric materials such as polyesters, polyimides, and the like.

A mercapto group can also react with a solid support having a halocarbonyl group to form a carbonylthio-containing attachment group. Solid supports having halocarbonyl groups include, for example, chlorocarbonyl substituted polyethylene.

A mercapto group can also react with a solid support having a halocarbonyloxy group to form an oxycarbonylthio-containing attachment group. Solid supports having halocarbonyl groups include chloroformyl esters of polyvinyl alcohol.

Additionally, a mercapto group can react with a solid support having an ethylenically unsaturated group to form a thioether-containing attachment group. Suitable solid supports having an ethylenically unsaturated group include, but are not limited to, polymers and copolymers derived from butadiene.

An isocyanato group can react with a solid support having a hydroxy group to form a oxycarbonylimino-containing attachment group. Examples of solid support materials having hydroxy groups include, but are not limited to, polyvinyl alcohol, corona-treated polyethylene, hydroxy substituted esters of polymethacrylates or polyacrylates, and a polyvinyl alcohol coating on glass or polymeric film.

An isocyanate group can also react with a mercapto group to form a thiocarbonylimino-containing attachment group. Examples of solid support materials having a mercapto group include, but are not limited to, mercapto substituted esters of polymethacrylates or polyacrylates and glass treated with a mercaptoalkylsilane.

Additionally, an isocyanate group can react with a primary aromatic amino group, a secondary aromatic amino group, or a secondary aliphatic amino group to form an iminocarbonylimino-containing attachment group. Suitable solid supports having primary or secondary amino groups include, but are not limited to, polyamines, polyethylenimines, and coatings of an aminoalkylsilane on a support material such as glass or on a polymeric material such as a polyester or polyimide.

An isocyanate group can also react with a carboxy to form an O-acyl carbamoyl-containing attachment group. Suitable solid supports having a carboxylic acid group include, but are not limited to, a coating of an acrylic acid polymer or copolymer or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A halosilyl group, an alkoxysilyl group, or an acyloxysilyl group can react with a solid support having a silanol group to form a disiloxane-containing attachment group. Suitable solid supports include those prepared from various glasses, ceramic materials, or polymeric material. These groups can also react with various materials having metal hydroxide groups on the surface to form a siloxane-containing attachment group. Suitable metals include, but are not limited to, silver, aluminum, copper, chromium, iron, cobalt, nickel, zinc, and the like. In some embodiments, the metal is stainless steel or another alloy. Polymeric material can be prepared to have silanol groups. For example, commercially available monomers with silanol groups include 3-(trimethoxysilyl)propylmethacrylate and 3-aminopropyltrimethoxy silane from Aldrich Chemical Co., Milwaukee, Wis.

An azido group can react, for example, with a solid support having a carbon-carbon triple bond to form a triazolediyl-containing attachment group. An azido group can also react with a solid support having nitrile groups to form a tetrazinediyl-containing attachment group. Solid supports having nitrile groups include, but are not limited to, coatings of polyacrylonitrile on a support material such as glass or a polymeric material. Suitable polymeric support material includes polyesters and polyimides, for example. Other suitable solid supports having nitrile groups include acrylonitrile polymers or copolymers and 2-cyanoacrylate polymers or copolymers.

An azido group can also react with a strained olefinic group to form a triazolediyl-containing attachment group. Suitable solid supports having a strained olefinic group include coatings of materials having pendant norbornenyl groups. Suitable support materials include, but are not limited to, glass and polymeric materials such as polyesters and polyimides.

An aziridinyl group can react with a mercapto group to form a β-aminoalkylthioether attachment group. Examples of solid support materials having a mercapto group include, but are not limited to, mercapto substituted esters of polymethacrylates or polyacrylates and glass treated with a mercaptoalkylsilane.

Additionally, an aziridinyl group can react with a carboxy group to form a β-aminoalkyloxycarbonyl-containing attachment group. Suitable solid supports having a carboxy include, but are not limited to, a coating of an acrylic acid polymer or copolymer or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A haloalkyl group can react, for example, with a solid support having a tertiary amino group to form a quaternary ammonium-containing attachment group. Suitable solid supports having a tertiary amino group include, but are not limited to, polydimethylaminostyrene or polydimethylaminoethylmethacrylate.

Likewise, a tertiary amino group can react, for example, with a solid support having a haloalkyl group to form a quaternary ammonium-containing attachment group. Suitable solid supports having a haloalkyl group include, for example, coatings of a haloalkylsilane on a support material. Support materials can include, but are not limited to, glass and polymeric materials such as polyesters and polyimides.

A primary aromatic amino or a secondary aromatic amino group can react, for example, with a solid support having isocyanate group to form an oxycarbonylimino-containing attachment group. Suitable solid supports having isocyanate groups include, but are not limited to, a coating of a 2-isocyanatoethylmethacrylate polymer or copolymer on a glass or polymeric support. Suitable polymeric supports include polyesters, polyimides, and the like.

A primary aromatic amino or a secondary aromatic amino group can also react with a solid support containing a carboxy or halocarbonyl group to form a carbonylimino-containing attachment group. Suitable solid supports include, but are not limited to, acrylic or methacrylic acid polymeric coatings on a support material. The support material can be, for example, glass or a polymeric material such as polyesters or polyimides. Other suitable solid supports include copolymers of polyethylene and polymethacrylic acid or polyacrylic acid.

A disulfide, a thiol, or an alkyl disulfide group can react, for example, with a surface containing a metal or metal oxide. Suitable metals or metal oxides include, but are not limited to, gold, silver, platinum, palladium, nickel, copper, and chromium. The solid support can also be an alloy such as indium tin oxide or a dielectric material.

A benzotriazolyl can react, for example, with a solid support having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

A phosphono, phosphoroamido, or phosphato can react, for example, with a solid support having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

An ethylenically unsaturated group can react, for example, with a solid support having a mercapto group. The reaction forms a heteroalkylene-containing attachment group. Suitable solid supports include, for example, mercapto-substituted alkyl esters of polyacrylates or polymethacrylates.

An ethylenically unsaturated group can also react with a solid support having a silicon surface, such as a silicon solid support formed using a chemical vapor deposition process. Such silicon surfaces can contain —SiH groups that can react with the ethylenically unsaturated group in the presence of a platinum catalyst to form an attachment group with Si bonded to an alkylene group.

Additionally, an ethylenically unsaturated group can react with a solid support having a carbon-carbon double bond to form an alkylene-containing attachment group. Such solid supports include, for example, polymers or copolymers derived from butadiene.

Many other solid support materials and/or surface reactive groups are known and can be used if desired. Various combinations of solid support materials and/or surface reactive groups can be used if desired.

Biomolecule-Binding Groups
Aromatic Functional Biomolecule-Binding Groups

Biomolecule-binding groups function to assemble one or more polypeptides (e.g., antibodies, antibody conjugates, and proteins such as avidin, streptavidin, and clumping factor) to a surface of a solid support material via noncovalent hydrophobic interactions The biomolecule-binding groups include one or more aromatic groups, including monoaryl, bis-aryl, tris-aryl group, which are capable of forming a noncovalent hydrophobic bond with a polypeptide (preferably an antibody). Preferably, the biomolecule-binding groups include a plurality of aromatic groups. The aromatic (i.e., aryl) groups may or may not include heteroatoms (particularly, S, N, O) and they may or may not include substituents (e.g., hydroxyl, carboxyl, methoxy, methyl, amino, etc.).

For certain embodiments, the biomolecule-binding groups are disposed on at least 25% of the area of the surface of the solid support material. Also, it is preferred that the aromatic groups be sufficiently available on the surface to provide sufficient contact with the polypeptides of interest.

It is preferred that a biomolecule binding-group have a specific affinity for a specific polypeptide (preferably antibody, and more preferably an IgG antibody), although it is within the scope of the present invention to include a biomolecule-binding group that has multiple binding sites for a variety of different polypeptides (preferably antibodies, and more preferably IgG antibodies). It is also within the scope of the present invention to include multiple biomolecule-binding groups for a variety of different polypeptides (preferably antibodies, and more preferably IgG antibodies) on any one surface.

The size of the aryl group should be balanced against the number and type of hydrophilic groups, particularly if the solid support is particulate to avoid excessive agglomeration. If the aryl group is substituted, the substituents (e.g., hydroxyl, carboxyl, methoxy, methyl, amino groups) should not interfere sterically or electronically with the function of the biomolecule-binding group. If desired, the aryl groups can be substituted with hydrophilic groups, particularly to assist in the dispersion of particulate solid support material.

The aromatic groups may be covalently bonded to the solid support surface or they may be provided by a primer used to treat the solid support surface. The primer may or may not be covalently bonded to the solid support surface.

An example of immobilization of an antibody (represented by a Y-shaped molecule), which may or may not be oxidized, by a bis-aryl group through a noncovalent, hydrophobic mechanism, is shown below in Scheme I.

Antibody Immobilization:
Orientation Control

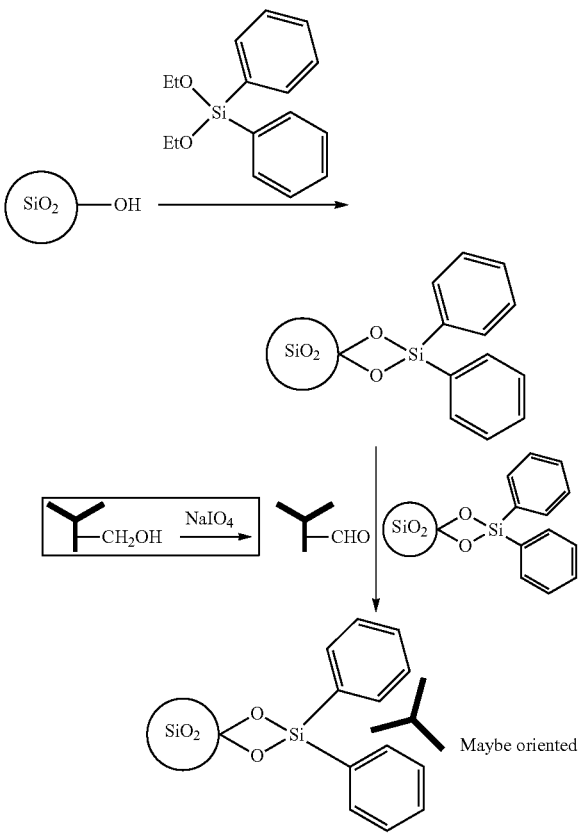

As used herein, the term "biomolecule-binding compound" describes a compound that can react with the surface of the solid support material to functionalize it with biomolecule-binding groups. It can be represented by the formula A-L-B, wherein A are the surface-bonding groups, which may be the same or different as other surface-bonding groups described herein, B represents the biomolecule-binding groups, and L represents an organic linker or a bond. Organic linkers L can be linear or branched alkylene, arylene, or a combination of alkylene and arylene groups, optionally including heteroatoms. For certain embodiments, the L groups do not include divalent alkylene oxide-containing oligomeric or polymeric groups. For certain embodiments, if the L groups do include divalent alkylene oxide-containing oligomeric or polymeric groups that could provide shielding and/or hydrophilic characteristics to the solid support material, they are not the only shielding and/or hydrophilic groups present on the solid support material.

Suitable surface-bonding groups A of the biomolecule-binding compounds (A-L-B) are described herein in the section entitled Solid Support Material. Examples include silanols, alkoxysilanes, or chlorosilanes for silica-containing surfaces, carboxylic acid or phosphoric acid groups for iron oxide-containing surfaces, mercaptans for gold-containing surfaces, carboxylic acid, phosphoric acid, triazolyl, or benzotriazolyl, groups for silver- or copper-containing surfaces, carboxylic acid groups for nylon-containing surfaces, amino groups for polyester-containing surfaces, carboxylic acid groups for cellulose nitrate-containing surfaces, and nitrene groups for polystyrene-containing surfaces.

Preferred biomolecule-binding compounds include diphenyl silane or triphenyl silane where the silane groups are alkoxysilane and/or chlorosilane. Those of ordinary skill in the art will recognize that a wide variety of other biomolecule-binding compounds are useful in the present invention as compounds that can be used to functionalize the solid support material with biomolecule-binding groups. Exemplary conditions for reacting such compounds with a solid support material are shown in the Examples Section. Preferably, a sufficient amount of biomolecule-binding compound is reacted with the solid support material to provide the desired level of attachment of biomolecule of interest (a polypeptide such as an antibody, preferably an IgG antibody).

Preferably, an antibody is attached to one or more aromatic groups through the Fc region of the antibody. More preferably, an antibody is attached to two or more of a plurality of aromatic groups through the Fc region of the antibody.

Aryl-Amine and Aryl-Hydrazine Biomolecule-Binding Groups

Biomolecule-binding groups function to covalently bond one or more biomolecules to a surface of a solid support material. It is preferred that a biomolecule binding-group have a specific affinity for a specific biomolecule, although it is within the scope of the present invention to include a biomolecule-binding group that has multiple binding sites for a variety of different biomolecules. It is also within the scope of the present invention to include multiple biomolecule-binding groups for a variety of different biomolecules on any one surface.

The biomolecule-binding group includes an aryl amine and/or an aryl hydrazine. The amine may be primary or secondary (i.e., nontertiary), although it is preferably a primary amine.

The biomolecule-binding groups can be provided by biomolecule-binding compounds represented by the formula A-L-B. The biomolecule-binding group B is an aryl nontertiary amine and/or aryl hydrazine group. Generally, the group B will be different from the group A (surface-bonding group). In this representation, L can be a bond or any of a variety of organic linkers, such that certain preferred groups L-B (or simply B) have the following structures:

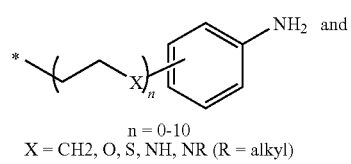

n = 0-10
X = CH2, O, S, NH, NR (R = alkyl)

-continued

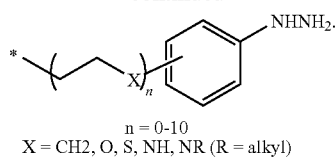

n = 0-10
X = CH2, O, S, NH, NR (R = alkyl)

For certain embodiments, the B group includes an aryl amine and/or aryl hydrazine and reacts with a biomolecule having a free carbonyl group through a Schiff base mechanism, thereby forming a linkage of the formula —Ar—N═C(H)-biomolecule, or —Ar—NHN═C(H)-biomolecule wherein Ar is an aryl group, which may be unsubstituted or substituted. The aryl group may include a single aromatic ring or multiple aromatic rings, which may or may not include heteroatoms (particularly, S, N, O). Examples include naphthalene, anthracene, pyrene, and biphenyl. If the aryl group is substituted, the substituents (e.g., hydroxyl, carboxyl, methoxy, methyl, amino groups) should not interfere sterically or electronically with the function of the aryl amine and/or aryl hydrazine as the biomolecule-binding group.

The size of the aryl group should be balanced against the number and type of hydrophilic groups (if present) to avoid excessive agglomeration if the solid support material is in particulate form. If desired, the aryl group can be substituted with hydrophilic groups to assist in the dispersion of particulate solid support material.

The biomolecule that attaches directly to the biomolecule-binding group is an aldehyde-functional biomolecule. If the biomolecule is an antibody, it is an oxidized antibody. Exemplary conditions for oxidation of antibodies are described in the Examples Section. Preferably the free carbonyl group is from the Fc region of the antibodies.

An example of immobilization of a biomolecule, such as an oxidized antibody (represented by a Y-shaped molecule), to an aryl amine through a Schiff base mechanism, is shown below in Scheme II.

Antibody Immobilization:
Orientation Control

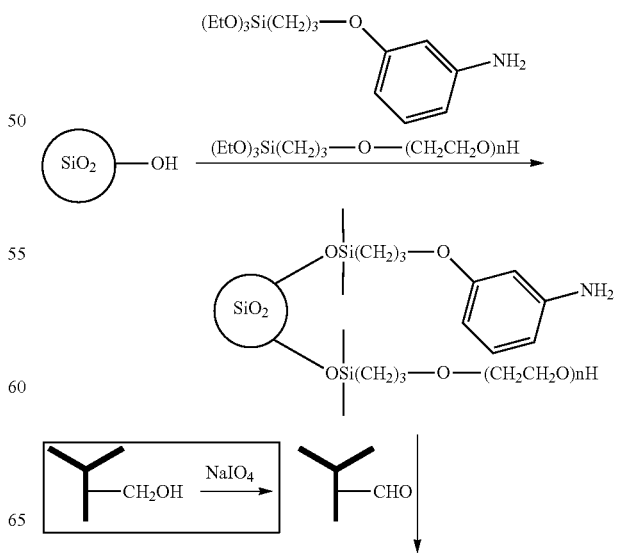

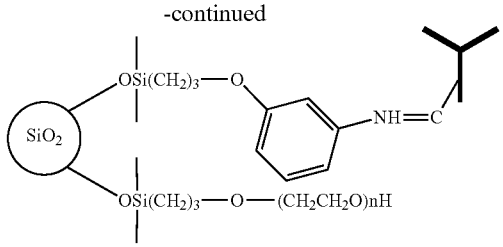

As used herein, the term "biomolecule-binding compound" describes a compound that can react with the surface of the solid support material to functionalize it with biomolecule-binding groups. It can be represented by the formula A-L-B, wherein A are the surface-bonding groups, which may be the same or different as other surface-bonding groups described herein, B represents the biomolecule-binding groups, and L represents an organic linker or a bond. Organic linkers L can be linear or branched alkylene, arylene, or a combination of alkylene and arylene groups, optionally including heteroatoms. For certain embodiments, the L groups do not include divalent alkylene oxide-containing oligomeric or polymeric groups. For certain embodiments, if the L groups do include divalent alkylene oxide-containing oligomeric or polymeric groups that could provide shielding and/or hydrophilic characteristics to the solid support material, they are not the only shielding and/or hydrophilic groups present on the solid support material.

Suitable surface-bonding groups A of the biomolecule-binding compounds are described herein in the section entitled Solid Support Material. Examples include silanols, alkoxysilanes, or chlorosilanes for silica-containing surfaces, carboxylic acid or phosphoric acid groups for iron oxide-containing surfaces, mercaptans for gold-containing surfaces, carboxylic acid or phosphoric acid groups for silver- or copper-containing surfaces, carboxylic acid groups for nylon-containing surfaces, amino groups for polyester-containing surfaces, carboxylic acid groups for cellulose nitrate-containing surfaces, and nitrene groups for polystyrene-containing surfaces.

Examples of biomolecule-binding compounds (i.e., compounds capable of providing a biomolecule-binding group having an aryl amine and/or aryl hydrazine group), represented by the formula A-L-B, include 4-aminophenyltrimethoxy silane. Those of ordinary skill in the art will recognize that a wide variety of other biomolecule-binding compounds are useful in the present invention as compounds that can be used to functionalize the solid support material with biomolecule-binding groups. Exemplary conditions for reacting such compounds with a solid support material are shown in the Examples Section. Preferably, a sufficient amount of biomolecule-binding compound is reacted with the solid support material to provide the desired level of attachment of biomolecule of interest (an oxidized polypeptide such as an oxidized antibody, preferably an IgG antibody).

Alpha,Beta Ethylenically or Acetylenically Unsaturated Biomolecule Binding Groups Biomolecule-binding groups function to covalently bond one or more biomolecules to a surface of a solid support material. It is preferred that a biomolecule binding-group have a specific affinity for a specific biomolecule, although it is within the scope of the present invention to include a biomolecule-binding group that has multiple binding sites for a variety of different biomolecules. It is also within the scope of the present invention to include multiple biomolecule-binding groups for a variety of different biomolecules on any one surface.

The biomolecule-binding group include an alpha,beta-ethylenically or acetylenically unsaturated group with an electron withdrawing group. Nonlimiting examples of electron withdrawing groups include carbonyls, ketones, esters, amides, —SO$_2$—, —SO—, —CO—CO—, —CO—COOR, sulfonamides, halides, trifluoromethyl, sulfonamides, halides, maleimides, maleates, or combinations thereof. For certain embodiments, the electron withdrawing groups is a ketone, ester, or amide.

The biomolecule-binding groups can be provided by biomolecule-binding compounds represented by the formula A-L-B. The biomolecule-binding group B includes an alpha,beta-ethylenically or acetylenically unsaturated group. Generally, the group B will be different from the group A (surface-bonding group). In this representation, L can be a bond or any of a variety of organic linkers, such that certain preferred group L-B (or simply B) has the following structures:

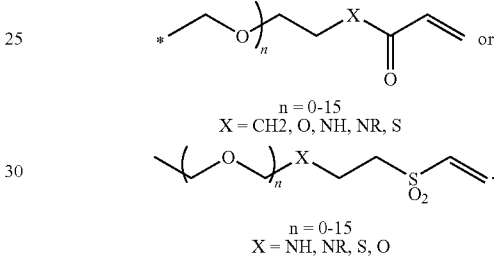

In certain embodiments the biomolecule-binding group includes an acrylate or an alpha,beta-unsaturated ketone. Acrylates and alpha,beta-unsaturated ketones exhibit the desirable properties of stability in water over a wide range of pH and yet also exhibit high reactivity with primary amines to irreversibly form a Michael addition adduct.

A Michael addition adduct results when an amino-group-bearing-biomolecule covalently bonds to a biomolecule-binding group by means of a carbon-nitrogen bond involving an amino group of the biomolecule and the beta position of an alpha,beta-ethylenically unsaturated group bearing a carbonyl unit at alpha position.

Scheme III below shows examples of acrylate compounds (which are examples of biomolecule-binding compounds), which are the starting materials used to react with and modify the surface of the solid support material in certain preferred embodiments. Such compounds are of the formula A-L-B wherein A is —Si(OR)$_3$ and B is the acrylate group:

SCHEME III

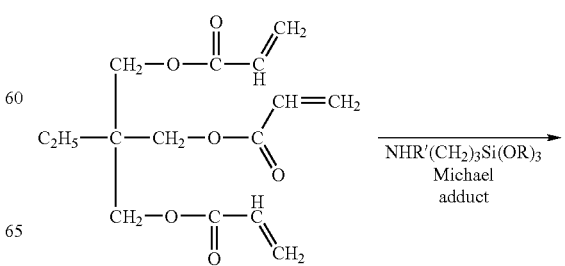

-continued

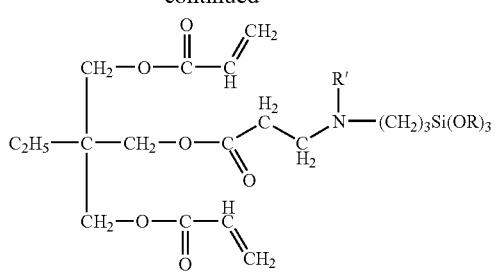

acrylic compound 1: R' = H; R = CH$_2$CH$_3$
acrylic compound 2: R' = CH3; R = CH$_3$

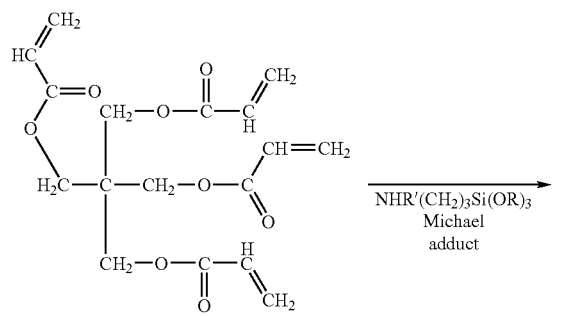

$\xrightarrow{\text{NHR'(CH}_2\text{)}_3\text{Si(OR)}_3}$
Michael adduct

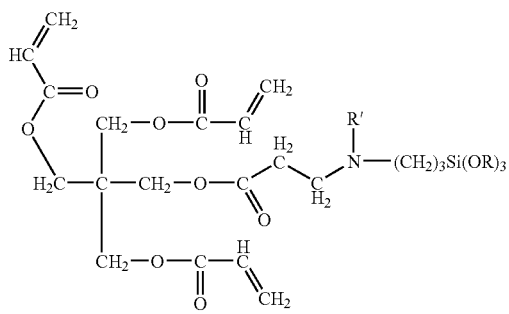

acrylic compound 3: R' = H; R = CH$_2$CH$_3$
acrylic compound 4: R' = CH3; R = CH$_3$ acrylic compound 5

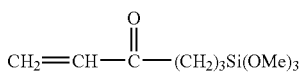

Acrylates and alpha,beta-unsaturated ketones are preferred because they are compatible with a wide variety of surface-bonding groups. In certain embodiments, the acrylate is multifunctional. As used herein, the term "biomolecule-binding compound" describes a compound that can react with the surface of the solid support material to functionalize it with biomolecule-binding groups. It can be represented by the formula A-L-B, wherein A are the surface-bonding groups, which may be the same or different as other surface-bonding groups described herein, B represents the biomolecule-binding groups, and L represents an organic linker or a bond. Organic linkers L can be linear or branched alkylene, arylene, or a combination of alkylene and arylene groups, optionally including heteroatoms. For certain embodiments, the L groups do not include divalent alkylene oxide-containing oligomeric or polymeric groups. For certain embodiments, if the L groups do include divalent alkylene oxide-containing oligomeric or polymeric groups that could provide shielding and/or hydrophilic characteristics to the solid support material, they are not the only shielding and/or hydrophilic groups present on the solid support material.

Other biomolecule-binding compounds include the following:

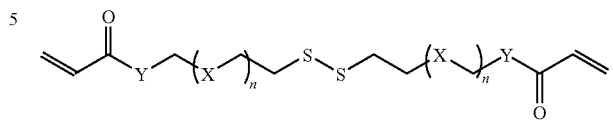

x = C, O, N, P, S
Y = C, O, N, S

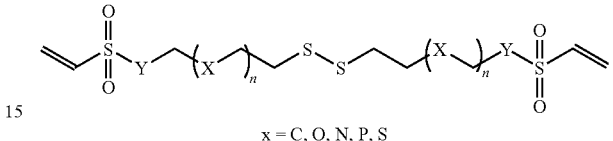

x = C, O, N, P, S
Y = C, O, N, S

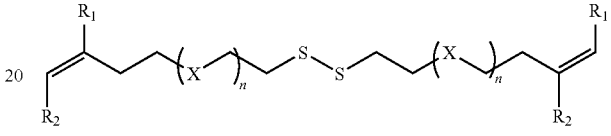

R1 and R2 are both electron-withdrawing groups
R1 = H, R2 = electron-withdrawing group
R2 = H, R1 = electron-withdrawing group wherein A is disulfide or mercapto surface-bonding groups, which can bind to Au and Ag, L is aliphatic or aromatic organic linkers, optionally containing heteroatoms and the biomolecule-binding group.

Suitable surface-bonding groups A of the biomolecule-binding compounds are described herein in the section entitled Solid Support Material. Examples include silanols, alkoxysilanes, or chlorosilanes for silica-containing surfaces, carboxylic acid or phosphoric acid groups for iron oxide-containing surfaces, mercaptans for gold-containing surfaces, carboxylic acid or phosphoric acid groups for silver- or copper-containing surfaces, carboxylic acid groups for nylon-containing surfaces, amino groups for polyester-containing surfaces, carboxylic acid groups for cellulose nitrate-containing surfaces, and nitrene groups for polystyrene-containing surfaces.

Examples of biomolecule-binding compounds include N-(3-acryloxy-2-hydroxypropyl)3-aminopropyl triethoxysilane, 3-acryloxypropyl trimethoxysilane, vinyl sulfone triethoxysilane-2,1,1,2-trifluorovinyl, 1,1,2-trichlorovinyl, 1,1-dichlorovinyl, 1,1-difluorovinyl, 1-fluoro or 1-chlorovinyl silanes, alpha,beta-unsaturated containing silanes, silane-containing quinones, alpha,beta-unsaturated ketones, sulfoxides, and alpha,beta-acetylenically unsaturated compounds having electron withdrawing groups. Those of ordinary skill in the art will recognize that a wide variety of other biomolecule-binding compounds are useful in the present invention as compounds that can be used to functionalize the solid support material with biomolecule-binding groups. Exemplary conditions for reacting such compounds with a solid support material are shown in the Examples Section. Preferably, a sufficient amount of biomolecule-binding compound is reacted with the solid support material to provide the desired level of attachment of biomolecule of interest (a polypeptide such as an antibody, preferably an IgG antibody).

Shielding Groups

"Shielding groups" are monovalent groups that are capable of reducing, and preferably preventing, nonspecific binding of biomolecules other than the target biological analyte (e.g., another biomolecule of interest). By monovalent, it is meant that the shielding groups do not have an end group that could react with, or immobilize, the biomolecule of interest. Certain of the hydrophilic groups described below may also function as shielding groups (e.g., poly(ethylene oxide)-containing groups, polyhydroxy-containing groups, sulfonic acid groups). The shielding groups are separate and distinct from the biomolecule-binding groups. That is, in certain embodiments the solid support materials include monovalent groups that provide shielding characteristics even though the same moiety may form a linker for the biomolecule-binding groups to the surface of the solid support material.

As used herein, the term "shielding compound" describes a compound that can react with the surface of the solid support material to modify it with shielding groups. It can be represented by the formula A-L-Sh, wherein A are the surface-bonding groups, which may be the same or different as other surface-bonding groups described herein, Sh represents the shielding groups, and L represents an organic linker or a bond. Organic linkers L can be linear or branched alkylene, arylene, or a combination of alkylene and arylene groups, optionally including heteroatoms.

The shielding group serves to block the binding of non-target analyte/biomolecule and bio-macromolecular materials to the surface of the solid support material and permits the solid support material to be used to bind, isolate, or immobilize specific biomolecules. The principal requirement of the shielding group is that it not bind a biomolecule of interest (e.g., capture agent or target biological analyte).

The shielding groups typically include, for example, non-ionic groups (such as poly(alkylene oxide)-containing groups, preferably poly(ethylene oxide)-containing groups, ethylene glycol ether-containing groups, poly(ethylene oxide) ether-containing groups, ethylene glycol lactate-containing groups, sugar-containing groups, polyol-containing groups, crown ether-containing groups, oligo glycidyl ether-containing groups including methyl ether and hydroxyethyl ether, hydroxyl acylamide-containing groups), anionic groups (e.g., sulfonate and carboxylate groups as described below as hydrophilic groups), and groups that are capable of forming an anionic group when dispersed in water (e.g., salts or acids). Various mixtures or combinations of such groups can be used if desired.

Preferably, a shielding group is an uncharged, water-soluble polymeric molecule of well defined length. Polymers of excessive length may have the effect of blocking the binding sites on the biomolecule-binding groups and thus their polymer length is preferably controlled.

Preferred shielding groups include, but are not limited to, poly(alkylene oxide)-containing groups (preferably short-chain oligomers having a molecular weight as low as 88, with a random or block structural distribution if at least two different moieties are included), ethylene glycol ether-containing groups, poly(ethylene oxide) ether-containing groups, ethylene glycol lactate-containing groups, sugar-containing groups, polyol-containing groups, crown ether-containing groups, oligo glycidyl ether-containing groups including methyl ether and hydroxyethyl ether, hydroxyl acylamide-containing groups (including oligomers and polymers of acrylamide), organosulfonate-containing groups, organocarboxylate-containing groups, or combinations thereof.

In some embodiments, a preferred shielding group is a poly(ethylene oxide)-containing group (preferably a macromonomer) that is monovalent, and has at least one —$CH_2$—$CH_2$—O— (repeat) unit, and may have —$CH(R^1)$—$CH_2$—O— (repeat) units, such that the macromonomer has a total of at least one, and preferably at least five, —$CH_2$—$CH_2$-β- (repeat) units, and the ratio of —$CH_2$—$CH_2$—O— units to —$CH(R^1)$—$CH_2$—O— units is at least 2:1 (preferably at least 3:1). If the poly(ethylene oxide)-containing groups also include —$CH(R^1)$—$CH_2$—O— groups, $R^1$ is a ($C_1$-$C_4$) alkyl group, which can be linear or branched. Thus, a small amount of propylene oxide (e.g., 0.2 mmol/gram of a nanoparticle) can be included in the poly(alkylene oxide) groups, although it is not desired.

Preferably, the molecular weight of the poly(ethylene oxide)-containing groups is at least 100 g/mole, more preferably at least 500 g/mole. It is generally preferred that they are limited in chain length such that they are less than the entanglement molecular weight of the oligomer. The term "entanglement molecular weight" as used in reference to the shielding group attached to the surface means the minimum molecular weight beyond which the polymer molecules used as the shielding group show entanglement. Methods of determining the entanglement molecular weight of a polymer are known, see for example Friedrich et al., Progress and Trends in Rheology V, Proceedings of the European Rheology Conference, 5th, Portoroz, Slovenia, Sep. 6-11, 1998 (1998), 387. Editor(s): Emri, I. Publisher: Steinkopff, Darmstadt, Germany. Preferably, the molecular weight of such polymeric groups is no greater than 10,000 grams per mole (g/mole).

While not meaning to suggest a mechanism for this preference, it is believed that short chain shielding groups are more suitable as opposed to long polymer chains to avoid blocking the binding sites of the biomolecule-binding group. It is reasonable to expect that short chain shielding groups will allow the biomolecule-binding sites to be accessible to the target analyte and/or capture agent. Longer chain shielding groups may block the biomolecule-binding groups, preventing any binding from occurring.

For certain embodiments, particularly if the solid support material includes carboxylate and/or sulfonate groups, there are preferably no poly(alkylene oxide) groups present on the solid support material as shielding or water-dispersible groups.

The surface density and identify of the shielding groups on a surface will depend on the desired efficiency of the overall system and method, taking into account a variety of factors such as cost of starting materials, the surface density and identity of the biomolecule-binding groups, the surface density and identity of the water-dispersible groups (if included), ease of synthesis, population density of the target analyte and/or capture agent in a sample of interest, and the sensitivity (e.g., signal to noise ratio) of the desired detection system. For example, the ratio of poly(ethylene oxide)-containing groups to amine-containing biomolecule-binding groups is at least 0.15:1 to prevent gelation (for nanoparticles); however for low nonspecific binding, the ratio of poly(ethylene oxide)-containing groups to amine-containing biomolecule-binding groups is at least 2:1.

Suitable surface-bonding groups A of the shielding compounds are described herein in the section entitled Solid Support Material. Examples include silanols, alkoxysilanes, or chlorosilanes for silica-containing surfaces, carboxylic acid or phosphoric acid groups for iron oxide-containing surfaces, mercaptans for gold-containing surfaces, carboxylic acid or phosphoric acid groups for silver- or copper-containing surfaces, carboxylic acid groups for nylon-containing surfaces, amino groups for polyester-containing surfaces, carboxylic acid groups for cellulose nitrate-containing surfaces, and nitrene groups for polystyrene-containing surfaces.

Examples of shielding compounds include poly(ethylene oxide) trimethoxysilane, $(OH)_3Si(CH_2)_3OCH_2CH(OH)$ $CH_2SO_3H$, and carboxylethyl silanetriol sodium salt. Those of ordinary skill in the art will recognize that a wide variety of other shielding compounds are useful in the present invention as compounds that can be used to modify the solid support material with shielding groups. Exemplary conditions for reacting such compounds with a solid support material are shown in the Examples Section. Preferably, a sufficient amount of shielding compound is reacted with the solid support material to provide the desired level of nonspecific binding without interfering with attachment of the biomolecule-binding groups.

Optional Hydrophilic (Water-Dispersible) Groups

Hydrophilic (e.g., water-dispersible) groups are monovalent groups that render the surface of the solid support material hydrophilic. This is desirable because they are also capable of increasing surface tension to reduce or eliminate dewetting issues when an aqueous biomolecule is attached. By monovalent, it is meant that the hydrophilic groups do not have an end group that could react with, or immobilize, the biomolecule of interest. Thus, the hydrophilic groups are separate and distinct from the biomolecule-binding groups. That is, in certain embodiments the solid support materials include monovalent groups that provide hydrophilic characteristics even though the same moiety may form a linker for the biomolecule-binding groups to the surface of the solid support material.

In certain embodiments, they are capable of reducing, and preferably preventing, excessive agglomeration and precipitation of the particles, particularly nanoparticles, in an aqueous buffer solution used in biological environments (although small amounts of agglomeration can be tolerated with the nanoparticles as long as the average size of the agglomerates is preferably no greater than 200 nm). Preferably, the water-dispersible nanoparticles are storage-stable in an aqueous buffer solution. By this it is meant that an aqueous dispersion of the water-dispersible nanoparticles is not subject to de-emulsification and/or coagulation or agglomeration at temperatures greater than 20° C., over a period of at least one year, when in a buffer.

As used herein, the term "hydrophilic compound" or "water-dispersible compound" describes a compound that can react with a surface of the solid support material to modify it with hydrophilic groups (e.g., water-dispersible groups). It can be represented by the formula A-L-WD, wherein A are the surface-bonding groups, which may be the same or different as other surface-bonding groups described herein, WD represents the hydrophilic (e.g., water-dispersible) groups, and L represents an organic linker or a bond. Organic linkers L can be linear or branched alkylene, arylene, or a combination of alkylene and arylene groups, optionally including heteroatoms.

The hydrophilic groups are water-like groups. They typically include, for example, nonionic groups, anionic groups, cationic groups, groups that are capable of forming an anionic group or cationic group when dispersed in water (e.g., salts or acids), or mixtures thereof.

Examples of nonionic hydrophilic groups include poly(alkylene oxide) groups and polyhydroxy-containing groups (including sugar-containing groups). A preferred nonionic hydrophilic group is a poly(alkylene oxide) group (preferably a macromonomer) that is monovalent, and has at least one $-CH_2-CH_2-O-$ (repeat) unit, and may have $-CH(R^1)-CH_2-O-$ repeat units, such that the macromonomer has a total of at least one, and preferably at least five, $-CH_2-CH_2-O-$ (repeat) units, and the ratio of $-CH_2-CH_2-O-$ repeat units to $-CH(R^1)-CH_2-O-$ repeat units is at least 2:1. Thus, a small amount of propylene oxide can be included in the poly(alkylene oxide) groups, although it is not desired.

The anionic or anion-forming groups can be any suitable groups that contribute to anionic ionization of the surface. For example, suitable groups include carboxylate groups ($-CO_2^-$ groups, including polycarboxylate), sulfate groups ($-SO_4^-$ groups, including polysulfate), sulfonate groups ($-SO_3^-$ groups, including polysulfonate), phosphate groups ($-PO_4^-$ groups, including polyphosphate), phosphonate ($-PO_3^-$ groups, including polyphosphonate), and similar groups, and acids thereof.

The cationic or cation-forming groups can be any suitable groups that contribute to cationic ionization of the surface. For example, suitable groups include quaternary ammonium, phosphonium, and sulfonium salts.

In certain embodiments, preferred hydrophilic groups include carboxylic acid groups, sulfonic acid groups, phosphonic acid groups, or combinations thereof.

The attachment of hydrophilic groups on the surface of a solid support material allows improved wettability of the solid material, and water-dispersibility of particles, particularly nanoparticles. Significantly, for nanoparticles such dispersions do not require external emulsifiers, such as surfactants, for stability. However, if desired anionic and cationic water-dispersible compounds can also be used in a composition that includes nanoparticles to function as an external emulsifier and assist in the dispersion of the nanoparticles.

The hydrophilic groups can be provided using hydrophilic compounds (A-L-WD). Suitable surface-bonding groups A of the hydrophilic compounds are described herein in the section entitled Solid Support Material. Examples include silanols, alkoxysilanes, or chlorosilanes for silica-containing surfaces, carboxylic acid or phosphoric acid groups for iron oxide-containing surfaces, mercaptans for gold-containing surfaces, carboxylic acid or phosphoric acid groups for silver- or copper-containing surfaces, carboxylic acid groups for nylon-containing surfaces, amino groups for polyester-containing surfaces, carboxylic acid groups for cellulose nitrate-containing surfaces, and nitrene groups for polystyrene-containing surfaces.

Some preferred hydrophilic compounds include the following:

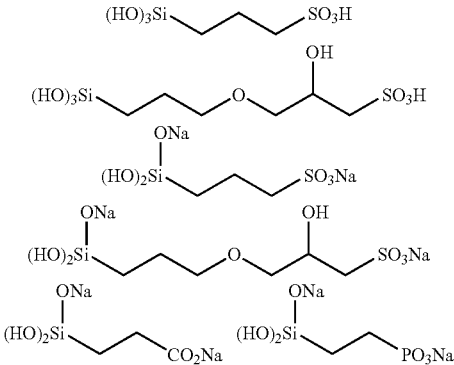

as well as other known compounds.

Those of ordinary skill in the art will recognize that a wide variety of other hydrophilic compounds are useful in the present invention as external emulsifiers or as compounds that can be used to modify the solid support material with hydrophilic groups. Exemplary conditions for reacting such compounds with a solid support material are analogous to the conditions used for reacting biomolecule-binding compounds and/or shielding compounds with a solid support material, as shown in the Examples Section.

Preferably, a sufficient amount of hydrophilic compound is reacted with the solid support material to provide the desired level of hydrophilicity without interfering with attachment of the biomolecule-binding groups. For example, for nanoparticles, the desired level of hydrophilicity is such that an external emulsifier is not necessary for preparing a storage-stable dispersion.

Optional Reporter Groups

The biomolecules of interest are typically detected by way of reporter groups (i.e., signaling groups) that provide a detectable signal. These reporter groups are typically attached directly to the surface of the solid support material (preferably through covalent bonds, and more preferably through nonreversible covalent bonds). The biomolecules could be quantified by first determining the amount of reporter groups in samples and then calculating the amount present using a set of standards to which the samples are compared.

Examples of such reporter group include luminescent groups including photoluminescent, particularly fluorescent groups. Examples of fluorescent reporter groups include coumarin, fluorescein, fluorescein derivatives, rhodamine, and rhodamine derivatives. Examples of luminescent reporter groups include adamantyl oxirane derivatives. Examples of chromogenic reporter groups include sulphonphthaleins, sulphonphthalein derivatives, and indoxyl compounds and their derivatives. Combinations of reporter groups can be used if desired. If particles are used as the solid support material, it be possible to use a combination of particles with different reporter groups. For example, one type of particle in a mixture could include an antibody with specificity "a" tagged with fluorescein and another type of particle could include an antibody with specificity "b" tagged with rhodamine. Thus, you could use a single assay to detect multiple antigens.

Although most of the reporter groups are designed to covalently bond directly to a solid support surface, it is possible to attach a reporter group to a solid support surface through another molecule (e.g., avidin) noncovalently. It is also possible to attach a fluorescent group (e.g., carboxyfluorescein and aminofluorescein) through ionic or hydrophobic interactions.

Preferably, the fluorescent reporter group is fluorescein such as that derived from a triethoxysilyl substituted fluorescein dye.

Reporter groups can be attached to the surface of a solid support material using a reporter compound (A-L-Rp), wherein Rp is the reporter group, A is a surface-bonding group, and L is an organic linker or a bond. Organic linkers L can be linear or branched alkylene, arylene, or a combination of alkylene and arylene groups, optionally including heteroatoms.

Suitable surface-bonding groups A of the reporter compounds (A-L-Rp) are described herein in the section entitled Solid Support Material. Examples include silanols, alkoxysilanes, or chlorosilanes for silica-containing surfaces, carboxylic acid or phosphoric acid groups for iron oxide-containing surfaces, mercaptans for gold-containing surfaces, carboxylic acid or phosphoric acid groups for silver- or copper-containing surfaces, carboxylic acid groups for nylon-containing surfaces, amino groups for polyester-containing surfaces, carboxylic acid groups for cellulose nitrate-containing surfaces, and nitrene groups for polystyrene-containing surfaces.

An example of a reporter compound is triethoxysilyl-substituted fluorescein. Those of ordinary skill in the art will recognize that a wide variety of other reporter compounds are useful in the present invention as compounds that can be used to modify the solid support material with reporter groups. Exemplary conditions for reacting such compounds with a solid support material are shown in the Examples Section. Preferably, a sufficient amount of reporter compound is reacted with the solid support material to provide the desired level of labeling.

Biomolecules

Biomolecules can be any chemical compound that naturally occurs in living organisms, as well as derivatives or fragments of such naturally occurring compounds. Biomolecules consist primarily of carbon and hydrogen, along with nitrogen, oxygen, phosphorus, and sulfur. Other elements sometimes are incorporated but are much less common. Biomolecules include, but are not limited to, proteins, antibodies, polypeptides, carbohydrates, polysaccharides, lipids, fatty acids, steroids, prostaglandins, prostacyclines, vitamins, cofactors, cytokines, and nucleic acids (including DNA, RNA, nucleosides, nucleotides, purines, and pyrimidines), metabolic products that are produced by living organisms including, for example, antibiotics and toxins. Biomolecules may also include derivatives of naturally occurring biomolecules, such as a protein or antibody that has been modified with chemicals (e.g., oxidized with sodium periodate). Biomolecules may also include crosslinked naturally occurring biomolecules, or a crosslinked product of a naturally occurring biomolecule with a chemical substance. Thus, as used herein, the term "biomolecule" includes, but is not limited to, both unmodified and modified molecules (e.g., glycosylated proteins, oxidized antibodies) and fragments thereof (e.g., protein fragments). Fragments of biomolecules can include those resulting from hydrolysis due to chemical, enzymatic, or irradiation treatments, for example.

In certain embodiments, biomolecules may be covalently bonded to one or more of the biomolecule-binding groups. In certain embodiments, the biomolecule can be modified to include an aldehyde group prior to its attachment to the biomolecule-binding group.

In some embodiments, the biomolecule that attaches directly to the biomolecule-binding group (whether it is the capture agent or the target biological analyte) includes or is modified to include an aldehyde group prior to its attachment to the biomolecule-binding group. Exemplary conditions for oxidizing antibodies to include an aldehyde group are disclosed in the Examples Section.

A biomolecule can include an entire organism (e.g., virus, bacterium) or a molecule within a cell or tissue or the organism. A "biomolecule of interest" can be a "capture agent," which can be used for "capturing" other biomolecules (e.g., an antibody for capturing a protein) or biomolecules within target biological analytes. Alternatively, a "biomolecule of interest" can be a "target analyte" (i.e., a "target biological analyte") or within a target analyte (e.g., a bacterium or other biomolecule of interest) for detection and/or analysis.

Capture Agents

The selective attachment of a target biological analyte may be achieved directly or it may be achieved through a capture agent, which is preferably an antibody, preferably captured using the Fc region of the antibody (e.g., where the target biological analyte itself includes the antigen bound to an antibody immobilized on the detection surface).

Capture agents include species (e.g., molecules, groups of molecules) that have high affinity for a target biological analyte, and preferably are specific for a target analyte. Capture agents include, for example, antibodies and fragments thereof (Fab, Fab', Fc), polypeptides, aptamers, DNA, RNA, oligo-nucleotides, proteins, antibodies, carbohydrates, polysaccharides, lipids, fatty acids, steroids, vitamins, cytokines, lectins, cofactors, and receptors (e.g., phage receptors). Capture agents may also include derivatives of naturally occurring biomolecules, such as a protein or antibody that has been modified with chemicals. These may also include crosslinked naturally occurring biomolecules, or a crosslinked product of a naturally occurring biomolecule with a chemical substance.

Preferred biomolecule capture agents suitable for use in the present invention include polypeptides including antibodies, antibody conjugates, and proteins such as avidin, streptavidin, and clumping factor). Particularly preferred biomolecule capture agents are antibodies. The term "antibody" is intended to include whole antibodies of any isotype (IgG, IgA, IgM, IgE, etc.), and fragments thereof from vertebrate, e.g., mammalian species, which are also specifically reactive with foreign compounds, e.g., proteins.

The antibodies can be monoclonal, polyclonal, or combinations thereof. Antibodies can be fragmented using conventional techniques and the fragments screened for utility in the same manner as whole antibodies. Thus, the term includes segments of proteolytically cleaved or recombinantly prepared portions of an antibody molecule that are capable of selectively reacting with a certain protein. Nonlimiting examples of such proteolytic and/or recombinant fragments include Fab, F(ab')$_2$, Fv, and single chain antibodies (scFv) containing a VL and/or VH domain joined by a peptide linker. The scFv's can be covalently or noncovalently linked to form antibodies having two or more binding sites. Antibodies can be labeled with any detectable moieties known to one skilled in the art. In some aspects, the antibody that binds to an analyte one wishes to measure (the primary antibody) is not labeled, but is instead detected indirectly by binding of a labeled secondary antibody or other reagent that specifically binds to the primary antibody.

Various *S. aureus* antibodies are known in the art. For example, *S. aureus* antibodies are commercially available from Sigma-Aldrich and Accurate Chemical. Further, other *S. aureus* antibodies, such as the monoclonal antibody Mab 12-9, are described in U.S. Pat. No. 6,979,446. In certain preferred embodiments, an antibody is selected from those described herein (e.g., selected from the group consisting of MAb-76, MAb-107, affinity-purified RxClf40, affinity-purified GxClf40, MAb 12-9), fragments thereof, or combinations thereof. Such antibodies are also disclosed in U.S. Patent No. 7,488,807 and entitled "ANTIBODY WITH PROTEIN A SELECTIVITY," and in U.S. Pat. Application Publication No. US2010/0047252 and entitled "ANTIBODY WITH PROTEIN A SELECTIVITY," and in PCT International Publication No WO2008/010580 and entitled "SPECIFIC ANTIBODY SELECTION BY SELECTIVE ELUTION CONDITIONS."

Preferred antibodies are monoclonal antibodies. Particularly preferred are monoclonal antibodies that bind to Protein A of *Staphylococcus aureus* (also referred to herein as "*S. aureus*" or "Staph A").

More particularly, in one embodiment suitable monoclonal antibodies, and antigen binding fragments thereof, are those that demonstrate immunological binding characteristics of monoclonal antibody 76 as produced by hybridoma cell line 358A76.1. Murine monoclonal antibody 76 is a murine IgG2A, kappa antibody isolated from a mouse immunized with Protein A. In accordance with the Budapest Treaty, hybridoma 358A76.1, which produces monoclonal antibody 76, was deposited on Oct. 18, 2006 in the American Type Culture Collection (ATCC) Depository, 10801 University Boulevard, Manassas, Va. 20110-2209, and was given Patent Deposit Designation PTA-7938 (also referred to herein as accession number PTA-7938). The hybridoma 358A76.1 produces an antibody referred to herein as "Mab 76." Mab 76 is also referred to herein as "Mab76," "Mab-76," "MAb-76," "monoclonal 76," "monoclonal antibody 76," "76," "M76," or "M 76," and all are used interchangeably herein to refer to immunoglobulin produced by hybridoma cell line 358A76.1 as deposited with the American Type Culture Collection (ATCC) on Oct. 18, 2006, and assigned Accession No. PTA-7938.

In another embodiment, suitable monoclonal antibodies, and antigen binding fragments thereof, are those that demonstrate immunological binding characteristics of monoclonal antibody 107 as produced by hybridoma cell line 358A107.2. Murine monoclonal antibody 107 is a murine IgG2A, kappa antibody isolated from a mouse immunized with Protein A. In accordance with the Budapest Treaty, hybridoma 358A107.2, which produces monoclonal antibody 107, was deposited on Oct. 18, 2006 in the American Type Culture Collection (ATCC) Depository, 10801 University Boulevard, Manassas, Va. 20110-2209, and was given Patent Deposit Designation PTA-7937 (also referred to herein as accession number PTA-7937). The hybridoma 358A107.2 produces an antibody referred to herein as "Mab 107." Mab 107 is also referred to herein as "Mab107," "Mab-107," "MAb-107," "monoclonal 107," "monoclonal antibody 107," "107," "M107," or "M 107," and all are used interchangeably herein to refer to immunoglobulin produced by the hybridoma cell line as deposited with the American Type Culture Collection (ATCC) on Oct. 18, 2006, and given Accession No. PTA-7937.

Suitable monoclonal antibodies are also those that inhibit the binding of monoclonal antibody MAb-76 to Protein A of *S. aureus*. The present invention includes monoclonal antibodies that bind to the same epitope of Protein A of *S. aureus* that is recognized by monoclonal antibody MAb-76. Methods for determining if a monoclonal antibody inhibits the binding of monoclonal antibody MAb-76 to Protein A of *S. aureus* and determining if a monoclonal antibody binds to the same epitope of Protein A of *S. aureus* that is recognized by monoclonal antibody MAb-76 are well known to those skilled in the art of immunology.

Suitable monoclonal antibodies are also those that inhibit the binding of monoclonal antibody MAb-107 to Protein A of *S. aureus*. The present invention includes monoclonal antibodies that bind to the same epitope of Protein A of *S. aureus* that is recognized by monoclonal antibody MAb-107. Methods for determining if a monoclonal antibody inhibits the binding of monoclonal antibody MAb-107 to Protein A of *S. aureus* and determining if a monoclonal antibody binds to the same epitope of Protein A of *S. aureus* that is recognized by monoclonal antibody MAb-107 are well known to those skilled in the art of immunology.

Suitable monoclonal antibodies are those produced by progeny or derivatives of this hybridoma and monoclonal antibodies produced by equivalent or similar hybridomas.

Also included in the present invention are various antibody fragments, also referred to as antigen binding fragments, which include only a portion of an intact antibody, generally including an antigen binding site of the intact antibody and thus retaining the ability to bind antigen. Examples of antibody fragments include, for example, Fab, Fab', Fd, Fd', Fv, dAB, and F(ab')$_2$ fragments produced by proteolytic digestion and/or reducing disulfide bridges and fragments produced from an Fab expression library. Such antibody fragments can be generated by techniques well known in the art.

Monoclonal antibodies useful in the present invention include, but are not limited to, humanized antibodies, chimeric antibodies, single chain antibodies, single-chain Fvs (scFv), disulfide-linked Fvs (sdFv), Fab fragments, F(ab') fragments, F(ab')$_2$ fragments, Fv fragments, diabodies, linear antibody fragments produced by a Fab expression library, fragments including either a VL or VH domain, intracellularly-made antibodies (i.e., intrabodies), and antigen-binding antibody fragments thereof.

Monoclonal antibodies useful in the present invention may be of any isotype. The monoclonal antibodies useful in the present invention may be, for example, murine IgM, IgG1, IgG2a, IgG2b, IgG3, IgA, IgD, or IgE. The monoclonal antibodies useful in the present invention may be, for example, human IgM, IgG1, IgG2, IgG3, IgG4, IgA1, IgA2, IgD, or IgE. In some embodiments, the monoclonal antibody may be murine IgG2a, IgG1, or IgG3. With the present invention, a given heavy chain may be paired with a light chain of either the kappa or the lambda form.

Monoclonal antibodies useful in the present invention can be produced by an animal (including, but not limited to, human, mouse, rat, rabbit, hamster, goat, horse, chicken, or turkey), chemically synthesized, or recombinantly expressed. Monoclonal antibodies useful in the present invention can be purified by any method known in the art for purification of an immunoglobulin molecule, for example, by chromatography (e.g., ion exchange, affinity, and sizing column chromatography), centrifugation, differential solubility, or by any other standard technique for the purification of proteins.

Suitable antibodies also include a high avidity anti-*Staphylococcus aureus* clumping factor protein polyclonal antibody preparation that detects recombinant clumping factor (rClf40) protein of *S. aureus* at a concentration of preferably at least 1 picogram per milliliter (pg/mL), and more preferably up to 100 pg/mL. Suitable antibodies also include a high avidity anti-*Staphylococcus aureus* clumping factor protein polyclonal antibody preparation demonstrating at least a 4-fold increase in detection sensitivity in comparison to a *Staphylococcus aureus* clumping factor protein antiserum.

In certain embodiments, a high avidity anti-*Staphylococcus aureus* clumping factor protein polyclonal antibody preparation is useful, wherein the high avidity anti-*S. aureus* clumping factor protein polyclonal antibody preparation is prepared by a method that includes obtaining antiserum from an animal immunized with recombinant clumping factor (rClf40) protein of *S. aureus*; binding the antiserum to a *S. aureus* clumping factor (Clf40) protein affinity column; washing the column with a wash buffer having 0.5 molar (M) salt and a pH of 4; and eluting the high avidity anti-*S. aureus* clumping factor protein polyclonal antibody preparation from the column with an elution buffer with a pH of 2. Herein, the high avidity anti-*Staphylococcus aureus* clumping factor polyclonal antibody preparations from rabbits and goats are referred to as affinity-purified RxClf40 and affinity-purified GxClf40, respectively. In some embodiments, the high avidity anti-*Staphylococcus aureus* clumping factor protein polyclonal antibody preparation may be obtained by a method that further includes enriching the antiserum for the IgG class of antibodies prior to binding the antiserum to a *S. aureus* clumping factor (Clf40) protein affinity column. Such enrichment may eliminate non-immunoglobulin proteins from the preparation and/or enrich for the IgG class of antibodies within the sample.

As used herein, antiserum refers to the blood from an immunized host animal from which the clotting proteins and red blood cells (RBCs) have been removed. An antiserum to a target antigen may be obtained by immunizing any of a variety of host animals. Any of a wide variety of immunization protocols may be used.

Antibody avidity is a measure of the functional affinity of a preparation of polyclonal antibodies. Avidity is the compound affinity of multiple antibody/antigen interactions. That is, avidity is the apparent affinity of antigen/antibody binding, not the true affinity. Despite the heterogeneity of affinities in most antisera, one can characterize such populations by defining an average affinity ($K_0$).

The surface coverage and packing of the capture agent on the surface may affect the sensitivity of detecting the target biological analyte. The immobilization chemistry that links the capture agent to the surface may play a role in the packing of the capture agents, preserving the activity of the capture agent, and may also contribute to the reproducibility and shelf-life of the surfaces. A variety of immobilization methods described elsewhere herein may be used in connection with surfaces to achieve the goals of high yield, activity, shelf-life, and stability.

Apart from the chemistry that binds to the capture agent and still keeps it active, there are other surface characteristics of any capture agent or immobilization chemistry used in connection with the present invention that may need to be considered and that may become relevant in clinical or environmental diagnostic applications. The immobilization chemistries should preferably cause limited or no interference with detection of the target bound to the surfaces. For example, the capture agent or immobilization chemistry should not interfere with (e.g., quench) the fluorescence emission of a fluorescent dye associated with the surface. The immobilization chemistry may also determine how the antibody or protein is bound to the surface and, hence, the orientation of the active site of capture. The immobilization chemistry may preferably provide reproducible characteristics to obtain reproducible data and sensitivity from the surfaces of the present invention.

Bioaffinity pairs, such as antigen/hapten, antibody/antigen binding fragment of the antibody, or complementary nucleic acids, bioreceptor/ligand (interleukin-4 and its receptor) may be used to attach capture agents. One of the pairs of such biomolecules is covalently attached to the biomolecule-binding agent. These biomolecules form part of a "capture agent" for a target biological analyte. For example, the strong bond formed between biotin and avidin and/or streptavidin may be particularly useful when attaching an antibody to a surface. Preferably, streptavidin can be used as a means to attach an antibody, to a surface. Streptavidin is a tetrameric protein isolated from *Streptomyces avidinii* that binds tightly to the vitamin biotin. Proteins, such as streptavidin, can be attached to surfaces through a number of chemistries.

Derivatives of biotin, such as N-hydroxysuccinimide esters of biotin (referred to as NHS-biotin), N-hydroxysulfosuccinimide esters of biotin (referred to as sulfo-NHS-biotin), sulfosuccinimidyl-6-[biotinamido]hexanoate (referred to as sulfo-NHS-LC-biotin), sulfosuccinimidyl-6-[biotinamido]-6-hexanamidohexanoate (referred to as sulfo-NHS-LC-LC-biotin), and N-hydroxysuccinimide PEG$_{12}$-biotins, and N-hydroxysuccinimide PEG$_4$-biotins (referred to as NHS-PEO$_{12}$-biotin or sulfo-NHS-PEO$_4$-biotin), can be used to attach biotins to biomolecules, such as antibodies, at primary amino acid groups. These biotinylated biomolecules can subsequently be attached to a surface that has streptavidin attached thereto.

Target Biological Analytes

"Target biological analytes" include, for example, tissues, cells, or biomolecules therewithin or derived therefrom (e.g., organism-specific antigens, enzymes, or other proteins, peptides, carbohydrates, toxins, or prions, cell wall components or fragments, flagella, pili, nucleic acids, antibodies).

As used herein, the term "tissue" refers to multicellular aggregates or organs derived from animals or plants, and include both viable and nonviable cells, connective tissue, and interstitial fluids. "Cell" refers to the basic structural and functional unit of all living organisms, including animals, plants, and single-celled microorganisms. As used herein, the term "microorganism" refers to prokaryotic or eukaryotic organisms that are generally classified as bacteria, viruses, yeast, filamentous fungi, and protozoa. As used herein, the term "prokaryotic organism" includes all forms of microorganisms considered to be bacteria including cocci, bacilli, spirochetes, sheroplasts, protoplasts, spores, etc.

Microbes (i.e., microorganisms) of particular interest include Gram positive bacteria, Gram negative bacteria, fungi, protozoa, mycoplasma, yeast, viruses, and even lipid-enveloped viruses. Particularly relevant organisms include members of the family Enterobacteriaceae, or genera *Staphylococcus* spp., *Streptococcus* spp., *Pseudomonas* spp., *Enterococcus* spp., *Esherichia* spp., *Bacillus* spp., *Listeria* spp., *Vibrio* spp., as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA), Vancomycin Resistant *Staphylococcus aureus* (VRSA), Vancomycin Intermediate-resistant *Staphylococcus aureus* (VISA)), *S. epidermidis*, *Streptococcus pneumoniae*, *S. agalactiae*, *S. pyogenes*, *Enterococcus faecalis*, Vancomycin Resistant *Enterococcus* (VRE), *Bacillus anthracis*, *Bacillus amyloliquefaciens*, *Bacillus amylolyticus*, *Bacillus cereus*, *Bacillus coagulans*, *Bacillus macerans*, *Bacillus megaterium*, *Bacillus polymyxa*, *Bacillus stearothermophillus*, *Bacillus subtilis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Vibrio cholera*, *V. parahemolyticus*, *Salmonella cholerasuis*, *S. typhi*, *S. typhimurium*, *Candida albicans*, *C. glabrata*, *C. krusei*, Strep A, Strep B, *Agrobacterium tumefaciens*, *Alcaligenes xylosoxydans* subsp. *denitrificans*, *Sphingomonas paucimobilis*, and multiple drug resistant Gram negative rods (MDR).

Gram positive and Gram negative bacteria are of interest. Of particular interest are Gram positive bacteria, such as *Staphylococcus aureus*. Typically, these can be detected by detecting the presence of a cell-wall component characteristic of the bacteria, such as a cell-wall protein. Also, of particular interest are antibiotic resistant microbes including MRSA, VRSA, VISA, VRE, and MDR. Typically, these can be detected by additionally detecting the presence of an internal cell component, such as a membrane protein.

Such microbes or other species of interest can be analyzed in a test sample that may be derived from any source, such as a physiological fluid, e.g., blood, saliva, ocular lens fluid, synovial fluid, cerebral spinal fluid, pus, sweat, exudate, urine, mucous, lactation milk, or the like. Further, the test sample may be derived from a body site, e.g., wound, skin, nares, scalp, nails, etc.

The art describes various patient sampling techniques for the detection of microbes such as *S. aureus*. Such sampling techniques are suitable for the method of the present invention as well. It is common to obtain a sample from wiping the nares of a patient. A particularly preferred sampling technique includes the subject's (e.g., patient's) anterior nares swabbed with a sterile swab or sampling device. For example, one swab is used to sample each subject, i.e., one swab for both nares. The sampling can be performed, for example, by inserting the swab (such as that commercially available from Puritan, East Grinstead, UK under the trade designation "Pure-Wraps") dry or pre-moistened with an appropriate solution into the anterior tip of the subject's nares and rotating the swab for two complete revolutions along the nares' mucosal surface. The swab is typically then cultured directly or extracted with an appropriate solution typically including water optionally in combination with a buffer and at least one surfactant.

Besides physiological fluids, other test samples may include other liquids as well as solid(s) dissolved in a liquid medium. Samples of interest may include process streams, water, soil, plants or other vegetation, air, surfaces (e.g., contaminated surfaces), and the like.

The test sample (e.g., liquid) may be subjected to prior treatment, such as dilution of viscous fluids. The test sample (e.g., liquid) may be subjected to other methods of treatment prior to injection into the sample port such as concentration, filtration, centrifugation, distillation, dialysis, dilution, filtration, inactivation of natural components, addition of reagents, chemical treatment, etc.

The methods of the present invention can involve not only detecting the presence of a biomolecule (e.g., microorganism or a biomolecule thereof), but preferably identifying said biomolecule. In certain embodiments, detecting the presence a biomolecule includes quantifying the biomolecule.

Methods of Making and Methods of Use

The surfaces of the solid support materials of the present invention can be modified in a variety of ways. Typically, compounds containing surface-bonding groups (e.g., silica-binding groups) and the desired biomolecule-binding groups, shielding groups, hydrophilic (e.g., water-dispersible) groups, and/or reporter groups can be contacted with the surface under conditions effective to covalently bond (preferably nonreversibly covalently bond) the groups to the surface of the solid support material. Exemplary such conditions are specified in the Examples Section. The typical order of addition involves attaching the shielding groups first, if they are used. Although it is believed that the order of addition is not critical, there could be some situations where adding the biomolecule-binding group first may prevent or affect binding the shielding group.

The modified solid support materials are then used to attach a biomolecule (e.g., a polypeptide). This is done under conditions effective to attach one or more biomolecules to the surface through the biomolecule-binding groups. The attachment of an antibody or other biomolecule typically takes place under mild conditions, and can occur under a broad pH range, preferably pH at 4-11, more preferably pH at 6-10, and most preferably pH at 7-9. The preferred temperature for attachment of an antibody or other biomolecule is room temperature. Also, lower or higher temperatures can be used, but not at temperatures which denature the biomolecule. This chemistry is suitable for all kinds of biological media, basic and even mildly acidic buffer solutions, and in mixed solvents including solvents such as DMSO or acetonitrile. Exemplary such conditions are specified in the Examples Section.

The biomolecule can be the desired target analyte, a within the target analyte, a portion of the target analyte, or it can be a capture agent for a target analyte (preferably specific for a particular target analyte), which is captured in a subsequent step. The interaction between the biomolecule and the biomolecule-binding group may be covalent (preferably nonreversibly covalently bond), the interaction between capture agent and the target analyte is not necessarily covalent. Although the interaction between the biomolecule and the biomolecule-binding group may be hydrophobic in some embodiments, the interaction between a polypeptide capture agent and a target analyte is not necessarily hydrophobic.

It will be understood that the methods of the present invention that include attachment of a biomolecule (whether it be a capture agent or a target analyte) to a surface that includes alpha,beta-unsaturated groups are typically not chromatographic methods that involve elution of the biomolecules from the surface subsequent to capture of such biomolecules. It will be further understood that the methods of the present invention that include attachment of an antibody or other polypeptide to a surface that includes one or more aromatic groups are typically not chromatographic methods that involve elution of the antibodies and/or other polypeptides and/or other target analytes from the surface subsequent to capture of such biomolecules.

EXAMPLES

Objects and advantages of this invention are further illustrated by the following examples, but the particular materials and amounts thereof recited in these examples, as well as other conditions and details, should not be construed to unduly limit this invention.

All parts, percentages, ratios, etc. in the examples are by weight, unless noted otherwise. Solvents and other reagents used were obtained from Sigma-Aldrich Chemical Company, St. Louis, Mo., or Alfa Aesar of Ward Hill, Mass., unless otherwise noted. Purified water, obtained from a MILLI-Q water system (Millipore, Billerica, Mass.), was used to prepare all aqueous solutions, unless otherwise noted.

Examples 1-6

*Staphylococcus aureus* Detection by Solid Support Material Modified with Biomolecule-Binding Groups but No Shielding Groups

*Staphylococcus aureus* antibody (YVS 6881) was obtained from the America Type Culture Collection (ATCC, Manassas, Va.). *Staphylococcus aureus* strain 6538 was obtained from the ATCC.

Glass slides were immersed in a solution of sulfuric acid (22.5 volume percent (vol-%)) and hydrogen peroxide (7.5 vol-%) in water (70 vol-%) for 30 minutes (min). After this soaking period, the glass slides were removed from the cleaning solution and subsequently washed with deionized water thoroughly. These cleaned glass slides were then dried at 120° C. prior to use.

Cleaned glass slides were immersed in a toluene solution containing phenyl silane, diphenyl diethoxysilane, or triphenyl chlorosilane (available from Gelest, Inc., Morrisville, Pa.) at several concentrations (as listed in Table 1) for 30 minutes at room temperature. The glass slides were washed with toluene to remove excess silane reagents, and then placed in an oven at 120° C. for 10 min. Each of the modified glass slides was incubated with 100 microliters of 100 micrograms per milliliter (µg/mL) YVS6881 antibody in phosphate buffered saline (PBS; 0.9% (weight/volume (w/v)) NaCl in 10 millimolar (mM) sodium phosphate, pH=7.4) at 4° C. for 14 hours. Subsequently, these slides were incubated with BSA (Bovine Serum Albumin) for 1 hour. Control sample slides were incubated with 100 microliters (µL) of 1 milligram per milliliter (mg/mL) Bovine Serum Albumin (BSA) in Phosphate Buffered Saline (PBS) for blocking of all of the binding sites. After incubation, the slides were thoroughly washed with PBS/Tween solution (PBS with 0.05% (w/v) Tween 20).

*S. aureus* strain 6538 bacteria were inoculated into Trypticase Soy Broth (TSB) medium and grown overnight (approximately 16 hours) at 37° C. The bacteria were harvested by centrifugation at 8000 revolutions per minute (rpm) for 8 minutes at 25° C. The bacterial pellet was washed with an equal volume of PBS/Tween, re-centrifuged, and the washed bacteria were resuspended in PBS to a concentration of approximately $10^8$ cells/mL. Subsequently the bacteria were incubated with dye Syto 9 (Molecular Probes/Invitrogen, Carlsbad, Calif.) (1.5 µL for every 1 mL of bacterial solution) for 15 minutes (min) at 25° C.

The prepared bacteria (100 microliters (µL) of bacteria solution) was applied to specified areas on the slide and incubated for 30 min. The final slides were thoroughly washed with PBS/Tween 20, and the images of the slides were taken with a Leica fluorescent microscope (Leica microscope models 512834/067793 or DMI6000B from Leica Microsystems Inc., Bannockburn, Ill.). Binding interaction between the nanoparticles and the bacteria was assessed by observing the suspensions microscopically under both ultraviolet and bright-field illumination. Positive binding interaction was affirmed when fluorescent spheres which were observed under ultraviolet light illumination coincided with the presence of spherical bacteria observed under bright-field illumination at the same location on the slide. Highly bright fluorescence was observed for almost every single bacterium or cluster of bacteria for samples using the polyphenyl surface-modified glass (over 90% of the area was covered with fluorescent labeled bacteria). Samples coated with phenyl silane ("medium fluorescence") exhibited about half as many bound fluorescent particles as those samples coated with polyphenylsilane-treated surfaces. Control samples, with BSA-treated glass, showed very low amounts of fluorescence (less than 5-10% of the area was covered with fluorescent labeled bacteria).

TABLE 1

| Example | Silane component | Wt-% in toluene | Bacterial binding capability |
|---|---|---|---|
| 1 | Phenyl silane | 2.0 | Medium |
| 2 | Diphenyl diethoxy silane | 0.5 | High |
| 3 | Diphenyl diethoxy silane | 1.0 | High |
| 4 | Diphenyl diethoxy silane | 2.0 | High |
| 5 | Triphenyl chlorosilane | 1.0 | High |
| 6 | Triphenyl chlorosilane | 2.0 | High |

Example 7

Preparation of Silica Nanoparticles Modified with Poly(Ethylene Oxide) Shielding Groups but No Biomolecule-Binding Groups A sample of 365 grams of NALCO 2327 silica (150 g, a 20-nanometer (20-nm) ammonia-stabilized silica particle, available from Nalco Co., Naperville, Ill.) at 40.88% solids in water was added to a reaction vessel. A sample of 30 grams of SILQUEST A-1230, a 500 molecular weight trimethoxysilane functional poly(ethylene oxide) (PEG-silane) from GE Silicones, was added to the reaction vessel. The solution was heated for 16 hours at 80° C. The reaction product was a clear fluid dispersion and included 0.4 millimolar (mmol) silane-substituted poly(ethylene oxide) oligomers per gram of 20-nm diameter silica nanoparticles.

Example 8

Preparation of Silica Nanoparticles Modified with Fluorescent Groups and Poly(Ethylene Oxide) Shielding Groups but No Biomolecule-Binding Groups A sample of 19.5 milligrams (mg) of fluorescein isothiocyanate (technical grade from Alfa Aesar, Ward Hill, Mass.) was added to a small vial. The dye was completely dissolved in 0.23 gram (g) of dry methyl sulfoxide (DMSO). A sample of 0.12 g of a 10% solution of 3-aminopropyltriethoxysilane in DMSO was added to the dye solution and reacted for 60 minutes at 60° C. to form a silane-functional fluorescein dye.

To an aqueous solution containing dispersed PEG-modified silica nanoparticles described above in Example 2 (58.5 g and 25 g of silica) was added the freshly prepared silane-functional fluorescein dye in DMSO. The mixture was subsequently heated for 16 hours at 60° C. to form fluorescein- and PEG-functional silica nanoparticles.

Examples 9-18

Effect of PEG-Silane with Sulfonated Silane or Carboxylated Silane, or Sulfonated Silane Alone on Nonspecific Binding of Nanoparticles without Biomolecule-Binding Groups For these examples, no biomolecule-binding groups were used in an effort to demonstrate the ability of PEG, sulfonate, and carboxylate groups to prevent or completely eliminate the nonspecific binding of biomolecules in the absence of any specific biomolecule binding.

Phosphate Buffered Saline (PBS) consisted of 0.9% (w/v) NaCl in 10 mM sodium phosphate, pH=7.4. PBS/TWEEN consisted of PBS containing 0.05% (weight/volume) TWEEN 20 (Sigma-Aldrich). Fluorescein isothiocyanate (FITC) was obtained from Molecular Probes/Invitrogen (Carlsbad, Calif.).

PEG-silane modified silica nanoparticles were prepared by the following general procedure: NALCO 2327 silica nanoparticles (1 gram, a 20-nm silica particle available from Nalco Co., Naperville, Ill.) at 40.0% solids in water was mixed with various amounts of PEG silane (poly(ethylene oxide) trimethoxy silane (PEG-silane), MW 500, available under the trade designation SILQUEST A-1230 from GE Silicones, Wilton, Conn.), sulfonated silane $((OH)_3Si(CH_2)_3OCH_2CH(OH)CH_2SO_3H)$, and carboxylated silane (carboxylethyl silanetriol sodium salt) as specified in Table 2. The amount of A-1230 PEG-silane was adjusted so the total silane charge (A-1230 PEG-silane+sulfonate silane) was 0.62 mmol silane/gram of nanosilica. The organosilane sulfonates were prepared exactly following procedures described in Example 1 of U.S. Pat. No. 4,338,377.

The above mixtures were reacted for 4-6 hours at 80° C. in a sealed reaction vessel. After the reaction, the resulting reaction mixture was placed in a SPECTRA/POR 2 dialysis membrane (12-14,000 molecular weight cutoff molecular porous membrane tubing from Spectrum Laboratories, Inc., Rancho Dominguez, Calif.). The membrane was placed in a vessel with continuous flowing deionized water for 20 hours.

The PEG-silane-modified silica nanoparticles at a concentration of $1 \times 10^{15}$ particles/mL were spun down at 13,000 rpm for 30 min. The collected nanoparticles were then resuspended in 200 microliters (μL) of PBS/TWEEN, and subsequently mixed with 100 micrograms per milliliter (μg/mL) each of fluorescein isothiocyanate-labeled Cytochrome C and fluorescein isothiocyanate-labeled Bovine Serum Albumin (obtained by the reaction of FITC dye molecules with the protein mixture for 2 hours at room temperature, following the standard fluorescein labeling procedure from Molecular Probes/Invitrogen, Carlsbad, Calif.). The resulting mixture was then incubated for 14 hours at 4° C. After the incubation period, the particles were separated by centrifuging at 13,000 rpm, for 30 min and redispersed in 1 mL PBS/TWEEN. This step was repeated three times. Five microliters (5 μL) of this dispersed nanoparticle solution were used to prepare samples to be observed using the microscope.

Fluorescent images were obtained by Leica Fluorescence Microscope, and were used to determine the degree of non-specific binding. Images having high fluorescence indicated high nonspecific binding (low is compared to the background, i.e., it is not much above the intensity for background; high is significantly above the background). The control experiments were conducted in a similar fashion, using untreated silica nanoparticles. The results are listed below in Table 2.

TABLE 2

| Example No. | Amount of organosilanol sulfonate and PEG silane in modified silica nanoparticles | Nonspecific binding |
|---|---|---|
| 9 | 50% PEG silane and 50% organosilanol sulfonate | Low |
| 10 | 32% PEG silane and 50% organosilanol sulfonate | Low |
| 11 | 16% PEG silane and 50% organosilanol sulfonate | Low |
| 12 | 50% organosilanol sulfonate $(OH)_3Si(CH_2)_3OCH_2CH(OH)CH_2SO_3H$ | Low |
| 13 | 75% organosilanol sulfonate $(OH)_3Si(CH_2)_3OCH_2CH(OH)CH_2SO_3H$ | Low |
| 14 | 100% organosilanol sulfonate $(OH)_3Si(CH_2)_3OCH_2CH(OH)CH_2SO_3H$ | Low |
| 15 | 50% PEG silane and 50% carboxylethyl silanetriol sodium salt | Low |
| 16 | 32% PEG silane and 50% carboxylethyl silanetriol sodium salt | Low |
| 17 | 15% PEG silane and 50% carboxylethyl silanetriol sodium salt | Low |
| 18 | Control-unmodified silica nanoparticles | High |

Example 9

Bacterial Capture Using an Oxidized Antibody Attached to Silica Nanoparticles Modified with Aryl Amine Biomolecule-Binding Groups and Poly(Ethylene Oxide) Shielding Groups Modified Nanoparticle Synthesis The 4-aminophenylsilane-attached silica nanoparticles were prepared by the following general procedure. A sample of NALCO 2327 silica (73.4 grams (g) available from Nalco Co., Naperville, Ill.) at 40.88% solids in water was diluted with 46.6 g of denatured ethanol. Poly(ethylene oxide) trimethoxysilane (3.0 g, SILQUEST A-1230 from GE Silicones, Wilton, Conn., 500 molecular weight) was added to the reaction vessel, resulting in a ratio of 0.2 millimole (mmol) of poly(ethylene oxide) trimethoxysilane per gram of nanosilica. The mixture was reacted for 16 hours (hrs) at 80° C. in a sealed reaction vessel to form PEG-modified silica. A sample (1.5 g) of this mixture was reacted with 0.3 mmol 4-aminophenyltrimethoxy silane (APS). The APS was diluted to 10% or 1% with ethanol and added to an aliquot of the PEG-modified silica in the desired amount. The dilution in ethanol was to assure accurate addition of small amounts of silane to the reaction. The reactants were placed in a sealed reaction vessel and reacted for 16 hrs at 80° C. Following this reaction an additional charge of A-1230 poly(ethylene oxide) trimethoxysilane was added to the reaction vessel. The A-1230 poly(ethylene oxide) trimethoxysilane charge was adjusted so the total silane charge (A-1230+APS) was 0.62 mmol silane/gram of nanosilica. The reaction vessel was resealed and placed in an 80° C. oven for 16 hrs. Next, the reaction mixture was placed in a SPECTRA/POR 2 dialysis membrane (12-14,000 molecular weight cutoff molecular porous membrane tubing from Spectrum Laboratories, Inc., Rancho Dominguez, Calif.). The membrane was placed in a vessel with continuous flowing deionized water for 16 hrs.

Oxidation of Antibodies (Anti S. Aureus) by $NaIO_4$

Staphylococcus aureus strain 6538 was obtained from the American Type Culture Collection (ATCC, Manassas, Va.). Polyclonal (rabbit) anti-S. aureus IgG antibody was obtained from Accurate Chemical & Scientific Corporation, Westbury, N.Y. Phosphate Buffered Saline (PBS) consisted of 0.9% (weight/volume (w/v)) NaCl in 10 millimolar (mM) sodium phosphate, pH=7.4. PBS/TWEEN consisted of PBS containing 0.05% (w/v) TWEEN 20 (Sigma-Aldrich Chemical Co., St. Louis, Mo.). A fluorescein-conjugated goat anti-rabbit antibody F(ab')2 IgG Fragment (H+L) was obtained from Jackson ImmunoResearch (West Grove, Pa.) under the trade designation AffiniPure.

Rabbit antibody IgG (anti-S. aureus, 0.5 milliliters (mL) of 4.8 mg/mL) was mixed with 2.5 mL buffer solution with pH=5 (0.02 molar (M) sodium acetate and 0.15 M NaCl), and the antibody solution was allowed to pass through an Econo-10DG desalting column (Pierce Chemical Company, Rockford, Ill.) buffer exchange. Three milliters (3 mL) of forerun from the column were rejected. Then the next seven 0.5-mL fractions, which each tested positive for the antibody, were pooled together.

The preparation of periodic acid reagent and the oxidation of the antibody were carried out in the dark in order to minimize light exposure. $NaIO_4$ solution (0.01 M) was added to the antibody solution. The antibody oxidation reaction was allowed to proceed at room temperature for 30 minutes (min). After the reaction, ethylene glycol (20 vol-%) was added to quench the reaction. The unreacted ethylene glycol and undesired oxidation byproducts, such as formaldehyde, were removed by centrifuging at 10,000 revolutions per minute (rpm) and discarding the supernatant. A CENRICON filter unit (Millipore) was first washed with 1 mL of purified water by spinning at 5000 rpm for 30 min, then reversing the filter and spinning at 1000 rpm to remove remaining water. Then a maximum of 1.1 mL of the oxidized solution was applied and centrifuged at 5000 rpm for 40 min. One millimeter (1 mL) of 25 mM phosphate buffer at pH=7.0 was added to further wash away the unreacted ethylene glycol and undesired oxidation byproducts, and the sample was then spun at 5000 rpm for 40 min. The oxidized antibody was transferred in an Eppendorf tube.

Antibody attachment to the aryl-amine-modified nanoparticles and bacteria binding evaluation The 4-aminophenyl trimethoxysilane and PEG-attached silica nanoparticles described above at concentrations of $10^{13}$ and $10^{14}$ particles/mL were reacted with oxidized antibody (50 micrograms (μg)) overnight at 4° C. The resulting particles were spun down at 13,000 rpm for 30 min, then the particles were washed 2× with PBS+0.05% TWEEN 20 for the removal of the unreacted antibody. In addition to the PEG, bovine serum albumin (BSA, 5 mg/mL) was utilized to block the nonspecific binding sites by exposure overnight at 4° C. The treated particles were washed twice with the PBS/TWEEN solution for the removal of excess BSA.

S. aureus ATCC 6538 (SA6358) was prepared by growing a culture overnight in TSB broth at 37° C., washing the cells twice in PBS/TWEEN, and resuspending the cells in an equal volume of PBS/TWEEN. The cells were washed by centrifuging at 8000 rpm for 8 min at room temperature to pellet the cells, and resuspending the cells in PBS/TWEEN. The washed bacterial concentration was approximately $10^8$ cells/mL, which was determined by absorption measurement at 670 nanometers (nm).

The mixture was washed twice by centrifugation. Fluorescein-conjugated Goat Anti-Rabbit IgG (H+L) was dissolved into 0.75 mL purified water (MILLI-Q, Millipore, Billerica, Mass.) and 0.75 mL of glycerol. Fluorescein-conjugated Goat Anti-Rabbit IgG (H+L) (50 micrograms/milliliter (μg/mL)) was introduced to the above incubation suspension containing the bacteria and antibody-tethered silica particles for labeling. This mixed solution was further incubated at room temperature for another 30 min. The samples were washed with purified water by centrifugation twice at 6000 rpm with 6-min spins. The resulting pellets were resuspended and viewed through a Leica Fluorescence microscope.

Binding interaction between the nanoparticles and the bacteria was assessed by observing the suspensions microscopically under both ultraviolet and bright-field illumination. Positive binding interaction between the nanoparticles and bacteria was affirmed when fluorescent spheres which were observed under ultraviolet light illumination coincided with the presence of spherical bacteria observed under bright-field illumination at the same location on the slide. Bright fluorescent labeling of bacteria (representative of a relatively high level of bacteria) was detected for those samples with modified nanoparticles. In contrast, very low or no fluorescent labeling (relative to background) was detected in control samples, where bovine serum albumin was used instead of antibody.

Example 10

Preparation of Silica Nanoparticles Modified with Fluorescent Groups and Poly(Ethylene Oxide) Shielding Groups but No Biomolecule-Binding Groups A sample of 365 grams of NALCO 2327 silica (150 g, a 20-nanometer (20-nm) ammonia-stabilized silica particle, available from Nalco Co., Naperville, Ill.) at 40.88% solids in water was added to a reaction vessel. A sample of 30 grams of SILQUEST A-1230, a 500 molecular weight trimethoxysilane functional poly(ethylene oxide) (PEG-silane) from GE Silicones, was added to the reaction vessel. The solution was heated for 16 hours at 80° C. The reaction product was a clear fluid dispersion and included 0.4 millimolar (mmol) silane-substituted poly(ethylene oxide) oligomers per gram of 20-nm diameter silica nanoparticles.

A sample of 19.5 milligrams (mg) of fluorescein isothiocyanate (technical grade from Alfa Aesar, Ward Hill, Mass.) was added to a small vial. The dye was completely dissolved in 0.23 gram (g) of dry methyl sulfoxide (DMSO). A sample of 0.12 g of a 10% solution of 3-aminopropyltriethoxysilane in DMSO was added to the dye solution and reacted for 60 minutes at 60° C. to form a silane-functional fluorescein dye.

To an aqueous solution containing dispersed PEG-modified silica nanoparticles described above (58.5 g and 25 g of silica) was added the freshly prepared silane-functional fluorescein dye in DMSO. The mixture was subsequently heated for 16 hours at 60° C. to form fluorescein- and PEG-functional silica nanoparticles.

Examples 11-20

Effect of PEG-Silane with Sulfonated Silane or Carboxylated Silane, or Sulfonated Silane Alone on Nonspecific Binding of Nanoparticles without Biomolecule-Binding Groups For these examples, no biomolecule-binding groups were used in an effort to demonstrate the ability of PEG, sulfonate, and carboxylate groups to prevent or completely eliminate the nonspecific binding of biomolecules in the absence of any specific biomolecule binding.

Phosphate Buffered Saline (PBS) consisted of 0.9% (w/v) NaCl in 10 mM sodium phosphate, pH=7.4. PBS/TWEEN consisted of PBS containing 0.05% (weight/volume) TWEEN 20 (Sigma-Aldrich). Fluorescein isothiocyanate (FITC) was obtained from Molecular Probes/Invitrogen (Carlsbad, Calif.).

PEG-silane modified silica nanoparticles were prepared by the following general procedure: NALCO 2327 silica nanoparticles (1 gram, a 20-nm silica particle available from Nalco Co., Naperville, Ill.) at 40.0% solids in water was mixed with various amounts of PEG silane (poly(ethylene oxide) trimethoxy silane (PEG-silane), MW 500, available under the trade designation SILQUEST A-1230 from GE Silicones, Wilton, Conn.), sulfonated silane (($OH)_3Si(CH_2)_3OCH_2CH(OH)CH_2SO_3H$), and carboxylated silane (carboxylethyl silanetriol sodium salt) as specified in Table 1. The amount of A-1230 PEG-silane was adjusted so the total silane charge (A-1230 PEG-silane+sulfonate silane) was 0.62 mmol silane/gram of nanosilica. The organosilane sulfonates were prepared exactly following procedures described in Example 1 of U.S. Pat. No. 4,338,377.

The above mixtures were reacted for 4-6 hours at 80° C. in a sealed reaction vessel. After the reaction, the resulting reaction mixture was placed in a SPECTRA/POR 2 dialysis membrane (12-14,000 molecular weight cutoff molecular porous membrane tubing from Spectrum Laboratories, Inc., Rancho Dominguez, Calif.). The membrane was placed in a vessel with continuous flowing deionized water for 20 hours.

The PEG-silane-modified silica nanoparticles at a concentration of $1 \times 10^{15}$ particles/mL were spun down at 13,000 rpm for 30 min. The collected nanoparticles were then resuspended in 200 microliters (μL) of PBS/TWEEN, and subsequently mixed with 100 micrograms per milliliter (μg/mL) each of fluorescein isothiocyanate-labeled Cytochrome C and fluorescein isothiocyanate-labeled Bovine Serum Albumin (obtained by the reaction of FITC dye molecules with the protein mixture for 2 hours at room temperature, following the standard fluorescein labeling procedure from Molecular Probes/Invitrogen, Carlsbad, Calif.). The resulting mixture was then incubated for 14 hours at 4° C. After the incubation period, the particles were separated by centrifuging at 13,000 rpm, for 30 min and redispersed in 1 mL PBS/TWEEN. This step was repeated three times. Five microliters (5 μL) of this dispersed nanoparticle solution were used to prepare samples to be observed using the microscope.

Fluorescent images were obtained by Leica Fluorescence Microscope, and were used to determine the degree of nonspecific binding. Images having high fluorescence indicated high nonspecific binding (low is compared to the background, i.e., it is not much above the intensity for background; high is significantly above the background). The control experiments were conducted in a similar fashion, using untreated silica nanoparticles. The results are listed below in Table 3.

TABLE 3

| Example No. | Amount of organosilanol sulfonate and PEG silane in modified silica nanoparticles | Nonspecific binding |
|---|---|---|
| 11 | 50% PEG silane and 50% organosilanol sulfonate | Low |
| 12 | 32% PEG silane and 50% organosilanol sulfonate | Low |
| 13 | 16% PEG silane and 50% organosilanol sulfonate | Low |
| 14 | 50% organosilanol sulfonate $(OH)_3Si(CH_2)_3OCH_2CH(OH)CH_2SO_3H$ | Low |
| 15 | 75% organosilanol sulfonate $(OH)_3Si(CH_2)_3OCH_2CH(OH)CH_2SO_3H$ | Low |
| 16 | 100% organosilanol sulfonate $(OH)_3Si(CH_2)_3OCH_2CH(OH)CH_2SO_3H$ | Low |
| 17 | 50% PEG silane and 50% carboxylethyl silanetriol sodium salt | Low |
| 18 | 32% PEG silane and 50% carboxylethyl silanetriol sodium salt | Low |
| 19 | 15% PEG silane and 50% carboxylethyl silanetriol sodium salt | Low |
| 20 | Control-unmodified silica nanoparticles | High |

Preparative Examples 21-24

Preparative Example 21

Acrylic alkoxysilane

Trimethylolpropanetriacrylate (TMPTA, 6.78 grams (g), 0.025 moles (mol) from Sartomer Company, Inc., Exton, Pa.) was dissolved in 25 milliliters (mL) of tetrahydrofuran (THF). The THF solution was stirred and cooled in an ice bath to 5° C. To the solution was slowly added 3-aminopropyltriethoxysilane (4.44 g, 0.020 mol). After addition, the solution was stirred for 1-2 hours (hrs) at the same conditions (i.e., in an ice bath at 5° C.). The solution was further stirred at room temperature for 1-2 hrs. After reaction, the THF was removed to give a clear viscous liquid. The reaction mixture (i.e., the clear viscous liquid) was sampled and analyzed by $^1$H NMR, which indicated the disappearance of 3-aminopropyltriethoxysilane and the presence of a mixture of desired secondary amine-based (as the major product) and tertiary amine-based (as a minor product) Michael adducts.

Preparative Example 22

Acrylic Alkoxysilane

TMPTA (5.42 g, 0.02 mol) was dissolved in 25 mL THF, and the THF solution was stirred and cooled in an ice bath to 5° C. To the solution was slowly added 3-(N-methyl)aminopropyltrimethoxysilane (3.86 g, 0.02 mol). After addition, the solution was stirred for 1-2 hrs at the same conditions (i.e., in an ice bath at 5° C.). The solution was further stirred at room temperature for 1-2 hrs. After reaction, the THF was removed to give a clear viscous liquid. The reaction mixture (i.e., the clear viscous liquid) was sampled and analyzed by $^1$H NMR, which indicated the disappearance of 3-(N-methyl)aminopropyltrimethoxysilane and the formation of the desired Michael adduct as a major component.

Preparative Example 23

Acrylic Alkoxysilane

Multifunctional acrylate SR-295 (8.18 g, 0.025 mol from Sartomer Company, Inc., Exton, Pa.) was dissolved in 25 mL THF. The solution was stirred and cooled in an ice bath to 5° C. To the solution was slowly added 3-aminopropyltriethoxysilane (4.44 g, 0.020 mol). After addition, the solution was stirred for 1-2 hrs under the same conditions (i.e., in an ice bath at 5° C.). The solution was further stirred at room temperature for 1-2 hrs. After reaction, the THF was removed to give a clear viscous liquid. The reaction mixture (i.e., the clear viscous liquid) was sampled and analyzed by $^1$H NMR, which indicated the disappearance of 3-aminopropyltriethoxysilane and the presence of a mixture of desired secondary amine-based (as the major product) and tertiary amine-based (as a minor product) Michael adducts.

Preparative Example 24

Acrylic Alkoxysilane

Multifunctional acrylate SR-295 (6.54 g, 0.02 mol) was dissolved in 25 mL THF. The solution was stirred and cooled in an ice bath to 5° C. To the solution was slowly added 3-(N-methyl)aminopropyltrimethoxysilane (3.86 g, 0.02 mol). After addition, the solution was stirred for 1-2 hrs at the same conditions (i.e., in an ice bath at 5° C.). The solution was further stirred at room temperature for 1-2 hrs. After reaction, the THF was removed to give a clear viscous liquid. The reaction mixture (i.e., the clear viscous liquid) was sampled and analyzed by $^1$H NMR, which indicated the disappearance of 3-(N-methyl)aminopropyltrimethoxysilane and the formation of the desired Michael adduct as a major component.

Examples 25-28

Preparation of Acrylated Silica Nanoparticles with PEG from Preparatory Examples 25-29

Acrylated silica nanoparticles were prepared by the following general procedure. NALCO 2327 silica nanoparticles (36.6 g, a 20-nm silica particle dispersion at 40.88% solids in water) were mixed with a poly(ethylene oxide) trimethoxy silane (SILQUEST A-1230 from GE Silicones, Wilton, Conn., 2.99 g or 3.74 g, mw=500) in a ratio of 0.40 mmol or 0.50 mmol of A-1230 silane per gram of 20-nm sized nanosilica. The mixture was reacted for 16 hours at 80° C. in a sealed reaction vessel to form modified silica. Aliquots of the modified silica prepared using 0.4 mmol A-1230 silane per gram silica were reacted with varying amounts (0.05 to 0.2 mmol silane per gram of nanosilica) of the acrylic compounds from Preparatory Examples 21-24. Each acrylic silane (diluted to 10% in THF) was added to an aliquot of the modified silica in the desired amount shown in Table 1. The reactants were placed in a sealed reaction vessel and reacted for 20 hours at 65° C. Following this, the reaction mixture was placed in a SPECTRA/POR 2 dialysis membrane (Rancho Dominguez, Calif.). The membrane was placed in a vessel with continuous flowing deionized water for 20 hours.

Antibody Attachment to Acrylated Silica Nanoparticles and Bacteria Binding

*Staphylococcus aureus* strain 6538 was obtained from the American Type Culture Collection (ATCC, Manassas, Va.). Polyclonal (rabbit) anti-*S. aureus* IgG antibody was obtained from Chemical & Scientific Corporation, Westbury, N.Y. Phosphate Buffered Saline (PBS) consisted of 0.9% (weight/volume (w/v)) NaCl in 10 millimolar (mM) sodium phosphate, pH=7.4. PBS/TWEEN 20 consisted of PBS containing 0.05% (w/v) TWEEN 20 (Sigma-Aldrich Chemical Co., St. Louise, Mo.). A fluorescein-conjugated goat anti-rabbit antibody F(ab')2 IgG Fragment (H+L) was obtained from Jackson ImmunoResearch, West Grove, Pa., under the trade designation AffiniPure.

Acrylate silica nanoparticles prepared as above at concentrations of $10^{13}$ and $10^{14}$ particles per milliliter were reacted with antibody IgG (rabbit polyclonal anti *Staph aureus* antibody, Chemical & Scientific Corporation, Westbury, N.Y.) overnight at 4° C. The resulting particles were spun down at 13,000 revolutions per minute (rpm) for 30 minutes (min), and then the particles were washed twice with PBS+0.05% TWEEN 20 for the removal of the unreacted antibody. After that, 2 mg/mL Bovine Serum Albumin (BSA) were added (as a carrier protein) and kept overnight at 4° C. Then the BSA-treated antibody-tethered particles were washed 2 times with PBS+TWEEN 20 (same as above) to remove excess BSA.

*S. aureus* ATCC 6538 (SA6358) was prepared by growing a culture overnight in TSB broth, washing the cells twice in PBS/TWEEN, and resuspending the cells in an equal volume of PBS/TWEEN. The cells were washed by centrifuging at 8000 rpm for 8 min at room temperature to pellet the cells, and resuspending the cells in PBS/TWEEN. The washed bacterial concentration was approximately $10^8$ cells/mL, which was determined by absorption measurement at 670 nm.

*S. aureus* 6538 bacteria at a concentration of $1\times10^8$ CFU/mL were allowed to incubate with the antibody-tethered silica particles for 30 min. The mixture was washed twice by centrifugation. Fluorescein-conjugated Goat Anti-Rabbit IgG (H+L) was dissolved into 0.75 mL purified water (MILLI-Q, Millipore, Billerica, Mass.) and 0.75 mL of glycerol. Fluorescein-conjugated Goat Anti-Rabbit IgG (H+L) (50 µg/mL) was introduced to the above incubation suspension containing the bacteria and antibody-tethered silica particles for labeling. This mixed solution was further incubated at room temperature for another 30 min. The samples were washed twice by centrifugation at 6000 rpm for 6 minutes each. The pellet was resuspended and viewed through a Leica Fluorescence microscope. The results are shown in Table 4.

Bright fluorescent labeling of bacteria was detected for the modified nanoparticles, which is representative of a relatively high level of bacterial capture. In contrast, very low or no fluorescence (relative to background) was detected for control samples, where bovine serum albumin was used instead of rabbit polyclonal anti-*Staphylococcus aureus* antibody. Comparable results were obtained from experiments conducted without the presence of BSA.

TABLE 4

| Example | Amount of acrylic silane and PEG silane in modified silica nanoparticles | Bacterial binding capability | Control |
|---|---|---|---|
| 25 | 1 g of 20 nm SiO$_2$ surface-covered with 0.1 mmol of acrylic silane Preparative Example-21 and 0.4 mmol of A1230 PEG silane | High | Low |
| 26 | 1 g of 20 nm SiO$_2$ surface-covered with 0.1 mmol of acrylic silane Preparative Example-22 and 0.4 mmol of A1230 PEG silane | High | Low |
| 27 | 1 g of 20 nm SiO$_2$ surface-covered with 0.1 mmol of acrylic silane Preparative Example-23 and 0.4 mmol of A1230 PEG silane | High | Low |

TABLE 4-continued

| Example | Amount of acrylic silane and PEG silane in modified silica nanoparticles | Bacterial binding capability | Control |
|---|---|---|---|
| 28 | 1 g of 20 nm $SiO_2$ surface-covered with 0.1 mmol of acrylic silane Preparative Example-24 and 0.4 mmol of A1230 PEG silane | High | Low |

Examples 29-46

Preparation of Functionalized Silica Nanoparticles

Silica nanoparticles attached with other functional groups were prepared by the following general procedure: 1.0 gram of NALCO 2327 silica nanoparticles (a 20-nm silica particle available from Nalco Co., Naperville, Ill.) at 40.0% solids in water was mixed with amounts of silanol #1, and silanol #2 as specified in Table 2. Poly(ethylene oxide) trimethoxy silane (MW 500, available under the trade designation SILQUEST A-1230) was obtained from GE Silicones, Wilton, Conn. The organosilane sulfonates were prepared essentially following procedures described in the Example 1 of U.S. Pat. No. 4,338,377. All others listed were obtained from Gelest, Inc., Morrisville, Pa.

The above mixture was reacted for 4-6 hours at 80° C. in a sealed reaction vessel. After the reaction, the resulting reaction mixture was placed in a SPECTRA/POR 2 dialysis membrane (12-14,000 molecular weight cutoff molecular porous membrane tubing from Spectrum Laboratories, Inc., Rancho Dominguez, Calif.). The membrane was placed in a vessel with continuous flowing deionized water for 20 hours.

Bacteria Binding Evaluation Procedure for Examples 29-46

*Staphylococcus aureus* strain 6538 was obtained from the American Type Culture Collection (ATCC, Manassas, Va.). Polyclonal (rabbit) anti-*S. aureus* IgG antibody was obtained from Accurate Chemical & Scientific Corporation, Westbury, N.Y. Phosphate Buffered Saline (PBS) consisted of 0.9% (w/v) NaCl in 10 mM sodium phosphate, pH=7.4. PBS/TWEEN consisted of PBS containing 0.05% (w/v) TWEEN 20 (Sigma-Aldrich). A fluorescein-conjugated goat anti-rabbit antibody F(ab')2 IgG Fragment (H+L) was obtained from Jackson ImmunoResearch (West Grove, Pa.) under the trade designation AffiniPure.

Silica nanoparticles prepared as above, at concentrations of $10^{13}$ and $10^{14}$ particles per milliliter, were reacted with antibody IgG mouse monoclonal anti-*Staph aureus* antibody ($3 \times 10^{14}$ antibody molecules, 75 µg of antibodies, from Strategic Diagnostics, Inc., Newark, Del.) overnight at 4° C. in PBS buffer solution (consisting of 0.9% (w/v) NaCl in 10 mM sodium phosphate, pH=7.4) with similar results. The antibody-conjugated particles were pelleted, washed twice with PBS/TWEEN, blocked with 2 mg/mL BSA, washed with centrifugation, resuspended in PBS/TWEEN as described in Examples 25-28 above. *S. aureus* 6538 at a concentration of $1 \times 10^8$ CFU/mL, and allowed to incubate with the antibody-tethered silica particles for 30 min. These suspensions were washed twice by centrifugation.

Fluorescein-conjugated Goat Anti-Rabbit IgG (H+L) was dissolved into 0.75 mL purified water (MILLI-Q, Millipore, Billerica, Mass.) and 0.75 mL of glycerol. Fluorescein-conjugated Goat Anti-Rabbit IgG (H+L) at 50 µg/mL was introduced to the above incubation suspension containing the bacteria and antibody-tethered silica particles for labeling. This mixed solution was further incubated for another 30 minutes.

The samples were washed and viewed through a Leica fluorescence microscope (Leica microscope models 512834/067793 or DMI6000B from Leica Microsystems Inc., Bannockburn, Ill.). Control samples were prepared using the same procedure as described above except that bovine serum albumin was used instead of antibody. The results are shown in Table 5.

Bacterial binding capability was determined by observing the particle suspensions through the microscope under conventional (bright-field) and ultraviolet (uv) illumination. Positive binding interaction of the nanoparticles with the bacteria was affirmed when fluorescent spheres which were observed under ultraviolet light illumination coincided with the presence of spherical bacteria observed under bright-field illumination at the same location on the slide. Bright fluorescent labeling of bacteria was detected for those samples with modified nanoparticles, which is representative of relatively high levels of captured bacteria. In contrast, very low or no fluorescence (relative to background) was detected in control samples, where bovine serum albumin was used instead of antibody.

TABLE 5

| Example No. | Silanol #1 and amount used | Silanol #2 and amount used | Bacteria binding capability |
|---|---|---|---|
| 29 | Carboxylethyl silanetriol sodium salt (0.32 mmol, 62.7 mg) | N-(3-acryloxy-2-hydroxypropyl) 3-aminopropyl triethoxysilane (0.2 mmol, 70 mg) | High |
| 30 | Carboxylethyl silanetriol sodium salt (0.32 mmol, 62.7 mg) | N-(3-acryloxy-2-hydroxypropyl) 3-aminopropyl triethoxysilane (0.1 mmol, 35 mg) | High |
| 31 | Carboxylethyl silanetriol sodium salt (0.32 mmol, 62.7 mg) | N-(3-acryloxy-2-hydroxypropyl) 3-aminopropyl triethoxysilane (0.05 mmol, 17.5 mg) | High |
| 32 | $(OH)_3Si(CH_2)_3OCH_2CH(OH)CH_2SO_3H$ (0.32 mmol, 88.3 mg) | N-(3-acryloxy-2-hydroxypropyl) 3-aminopropyl triethoxysilane (0.2 mmol, 70 mg) | High |
| 33 | $(OH)_3Si(CH_2)_3OCH_2CH(OH)CH_2SO_3H$ (0.32 mmol, 88.3 mg) | N-(3-acryloxy-2-hydroxypropyl) 3-aminopropyl triethoxysilane (0.1 mmol, 35 mg) | High |
| 34 | $(OH)_3Si(CH_2)_3OCH_2CH(OH)CH_2SO_3H$ (0.52 mmol, 143.5 mg) | N-(3-acryloxy-2-hydroxypropyl) 3-aminopropyl triethoxysilane (0.1 mmol, 35 mg) | High |
| 35 | $(OH)_3Si(CH_2)_3OCH_2CH(OH)CH_2SO_3H$ (0.32 mmol, 88.3 mg) | 3-acryloxypropyl trimethoxysilane (0.20 mmol, 46.8 mg) | High |
| 36 | $(OH)_3Si(CH_2)_3OCH_2CH(OH)CH_2SO_3H$ (0.32 mmol, 88.3 mg) | 3-acryloxypropyl trimethoxysilane (0.10 mmol, 22.9 mg) | High |
| 37 | $(OH)_3Si(CH_2)_3OCH_2CH(OH)CH_2SO_3H$ (0.52 mmol, 143.5 mg) | 3-acryloxypropyl trimethoxysilane (0.10 mmol, 23.2 mg) | High |
| 38 | Poly(ethylene oxide) trimethoxysilane (0.32 mmol, 160 mg) | Vinyl sulfone triethoxysilane-2 (0.31 mmol, 142.0 mg) | High |

TABLE 5-continued

| Example No. | Silanol #1 and amount used | Silanol #2 and amount used | Bacteria binding capability |
|---|---|---|---|
| 39 | Poly(ethylene oxide) trimethoxysilane (0.32 mmol, 160 mg) | Vinyl sulfone triethoxysilane-2 (0.2 mmol, 92 mg) | High |
| 40 | Poly(ethylene oxide) trimethoxysilane (0.32 mmol, 160 mg) | Vinyl sulfone triethoxysilane-2 (0.11 mmol, 52 mg) | High |
| 41 | Carboxylethyl silanetriol sodium salt (0.32 mmol, 62.7 mg) | Vinyl sulfone triethoxysilane-2 (0.31 mmol, 141 mg) | High |
| 42 | Carboxylethyl silanetriol sodium salt (0.32 mmol, 62.7 mg) | Vinyl sulfone triethoxysilane-2 (0.24 mmol, 108.0 mg) | High |
| 43 | Carboxylethyl silanetriol sodium salt (0.32 mmol, 62.7 mg) | Vinyl sulfone triethoxysilane-2 (0.1 mmol, 46.0 mg) | High |
| 44 | Carboxylethyl silanetriol sodium salt (0.4 mmol, 78.0 mg) | Vinyl sulfone triethoxysilane-1 (0.05 mmol, 17.0 mg) | High |
| 45 | $(OH)_3Si(CH_2)_3OCH_2CH(OH)CH_2SO_3H$ (0.32 mmol, 88.3 mg) | Vinyl sulfone triethoxysilane-1 (0.2 mmol, 68.0 mg) | High |
| 46 | $(OH)_3Si(CH_2)_3OCH_2CH(OH)CH_2SO_3H$ (0.50 mmol, 276.0 mg) | Vinyl sulfone triethoxysilane-1 (0.05 mmol, 17.0 mg) | High |

Examples 47-56

Effect of PEG-Silane with Sulfonated Silane or Carboxylated Silane, or Sulfonated Silane Alone on Nonspecific Binding of Nanoparticles without Biomolecule-Binding Groups For these examples, no biomolecule-binding groups were used in an effort to demonstrate the ability of PEG, sulfonate, and carboxylate groups to prevent or completely eliminate the nonspecific binding of biomolecules in the absence of any specific biomolecule binding.

Phosphate Buffered Saline (PBS) consisted of 0.9% (w/v) NaCl in 10 mM sodium phosphate, pH=7.4. PBS/TWEEN consisted of PBS containing 0.05% (weight/volume) TWEEN 20 (Sigma-Aldrich). Fluorescein isothiocyanate (FITC) was obtained from Molecular Probes/Invitrogen (Carlsbad, Calif.).

PEG-silane modified silica nanoparticles were prepared by the following general procedure: NALCO 2327 silica nanoparticles (1 gram, a 20-nm silica particle available from Nalco Co., Naperville, Ill.) at 40.0% solids in water was mixed with various amounts of PEG silane (poly(ethylene oxide) trimethoxy silane (PEG-silane), MW 500, available under the trade designation SILQUEST A-1230 from GE Silicones, Wilton, Conn.), sulfonated silane (($(OH)_3Si(CH_2)_3OCH_2CH(OH)CH_2SO_3H$), and carboxylated silane (carboxylethyl silanetriol sodium salt) as specified in Table 3. The amount of A-1230 PEG-silane was adjusted so the total silane charge (A-1230 PEG-silane+sulfonate silane) was 0.62 mmol silane/gram of nanosilica. The organosilane sulfonates were prepared exactly following procedures described in Example 1 of U.S. Pat. No. 4,338,377.

The above mixtures were reacted for 4-6 hours at 80° C. in a sealed reaction vessel. After the reaction, the resulting reaction mixture was placed in a SPECTRA/POR 2 dialysis membrane (12-14,000 molecular weight cutoff molecular porous membrane tubing from Spectrum Laboratories, Inc., Rancho Dominguez, Calif.). The membrane was placed in a vessel with continuous flowing deionized water for 20 hours.

The PEG-silane-modified silica nanoparticles at a concentration of $1\times10^{15}$ particles/mL were spun down at 13,000 rpm for 30 min. The collected nanoparticles were then resuspended in 200 microliters (μL) of PBS/TWEEN, and subsequently mixed with 100 micrograms per milliliter (μg/mL) each of fluorescein isothiocyanate-labeled Cytochrome C and fluorescein isothiocyanate-labeled Bovine Serum Albumin (obtained by the reaction of FITC dye molecules with the protein mixture for 2 hours at room temperature, following the standard fluorescein labeling procedure from Molecular Probes/Invitrogen, Carlsbad, Calif.). The resulting mixture was then incubated for 14 hours at 4° C. After the incubation period, the particles were separated by centrifuging at 13,000 rpm, for 30 min and redispersed in 1 mL PBS/TWEEN. This step was repeated three times. Five microliters (5 μL) of this dispersed nanoparticle solution were used to prepare samples to be observed using the microscope.

Fluorescent images were obtained by Leica Fluorescence Microscope, and were used to determine the degree of nonspecific binding. Images having high fluorescence indicated high nonspecific binding (low is compared to the background, i.e., it is not much above the intensity for background; high is significantly above the background). The control experiments were conducted in a similar fashion, using untreated silica nanoparticles. The results are listed below in Table 6.

TABLE 6

| Example No. | Amount of organosilanol sulfonate and PEG silane in modified silica nanoparticles | Nonspecific binding |
|---|---|---|
| 47 | 50% PEG silane and 50% organosilanol sulfonate | Low |
| 48 | 32% PEG silane and 50% organosilanol sulfonate | Low |
| 49 | 16% PEG silane and 50% organosilanol sulfonate | Low |
| 50 | 50% organosilanol sulfonate $(OH)_3Si(CH_2)_3OCH_2CH(OH)CH_2SO_3H$ | Low |
| 51 | 75% organosilanol sulfonate $(OH)_3Si(CH_2)_3OCH_2CH(OH)CH_2SO_3H$ | Low |
| 52 | 100% organosilanol sulfonate $(OH)_3Si(CH_2)_3OCH_2CH(OH)CH_2SO_3H$ | Low |
| 53 | 50% PEG silane and 50% carboxylethyl silanetriol sodium salt | Low |
| 54 | 32% PEG silane and 50% carboxylethyl silanetriol sodium salt | Low |
| 55 | 15% PEG silane and 50% carboxylethyl silanetriol sodium salt | Low |
| 56 | Control - unmodified silica nanoparticles | High |

Example 57

*Staphylococcus aureus* Detection by Surface Modified Glass

*Staphylococcus aureus* strain 6538 was obtained from the American Type Culture Collection (ATCC, Manassas, Va.).

Polyclonal (rabbit) anti-*S. aureus* antibody YVS6881) was obtained from Accurate Chemical & Scientific Corporation (Westbury, N.Y.). Phosphate Buffered Saline (PBS) consisted of 0.9% (w/v) NaCl in 10 mM sodium phosphate, pH, 7.4. PBS/TWEEN consisted of PBS containing 0.05% (w/v) TWEEN 20 (Sigma-Aldrich).

Glass slides were immersed in a solution of sulfuric acid (22.5 volume-%) and hydrogen peroxide (7.5 volume-%) in water (70 volume-%) for 30 min. After this soaking period, the glass slides were removed from the cleaning solution and subsequently washed with deionized water thoroughly. These cleaned glass slides were then dried at 120° C. prior to use.

Cleaned glass slides were individually immersed into methanol solutions containing a mixture of acrylic trialkoxysilane with A-1230 PEG-silane, at concentrations of 1-5 wt % in Table 4, for 30 min at 25° C. The resultant modified glass slides were incubated with *Staphylococcus aureus* antibody (YVS 6881 from Accurate Chemical & Scientific Corporation, Westbury, N.Y.), 100 μL of 100 μg antibody/1 mL of PBS) at 4° C. for 14 hours. Subsequently, these slides were incubated with BSA for 1 hour. Control sample slides were incubated with 100 μL of BSA solution only for blocking of all of the binding sites. After incubation, the slides were thoroughly washed with PBS buffer/TWEEN 20 solution (0.05% w/v).

*S. aureus* ATCC 6538 bacteria were grown, washed, and resuspended in PBS to a cell concentration of $10^8$ cells/mL, as described in Examples 25-28 above. Subsequently the bacteria were incubated with fluorescent dye Syto 9 (Molecular Probes, 3 μL for every 1 mL of bacterial solution) for 15 min at 25° C. Aliquots (100 microliters) of the fluorescent-stained bacteria were incubated with the above silane-treated slides for 30 min. The final slides were thoroughly washed PBS/TWEEN 20 (0.05% weight/volume) and the images of the slides were taken with a Leica fluorescent microscope (Leica microscope models 512834/067793 or DMI6000B from Leica Microsystems Inc., Bannockburn, Ill.). Fluorescent dots observed through the microscope or in the images, represented bacteria that were bound to the slide. The bacterial presence was confirmed by bright field illumination. Highly bright fluorescence was observed for almost every single bacterium, or bacteria with little clumps for samples using surface modified glass. Control sample, where Bovine Serum Albumin treated glass was very low amount of fluorescence was detected. The results are reported below in Table 7 ("Low" means less than 5-10% of the area was covered with fluorescent labeled bacteria; "High" means above 90% of the area was covered with fluorescent labeled bacteria).

TABLE 7

Glass slides covered by acrylic alkoxy silanes for covalently attaching IgG antibody for binding *S. aureus* bacteria

| Sample | Bacterial binding capability | Control |
|---|---|---|
| Preparative Example 57A:PEG = 1:99, N-(3-acryloxy-2-hydroxypropyl) 3-aminopropyl triethoxysilane (0.2 mmol, 70 mg) and PEG | High | Low |
| Preparative Example 57B:PEG = 5:95, N-(3-acryloxy-2-hydroxypropyl) 3-aminopropyl triethoxysilane (0.2 mmol, 70 mg) and PEG | High | Low |
| Preparative Example 57C:PEG = 1:99, 3-acryloxypropyl trimethoxysilane (0.10 mmol, 22.9 mg) and PEG | High | Low |
| Preparative Example 57D:PEG = 5:95, 3-acryloxypropyl trimethoxysilane (0.10 mmol, 22.9 mg) and PEG | High | Low |

Example 58

Preparation of Silica Nanoparticles Modified with Fluorescent Groups and Poly(Ethylene Oxide) Shielding Groups but No Biomolecule-Binding Groups A sample of 365 grams of NALCO 2327 silica (150 g, a 20-nanometer (20-nm) ammonia-stabilized silica particle, available from Nalco Co., Naperville, Ill.) at 40.88% solids in water was added to a reaction vessel. A sample of 30 grams of SILQUEST A-1230, a 500 molecular weight trimethoxysilane functional poly(ethylene oxide) (PEG-silane) from GE Silicones, was added to the reaction vessel. The solution was heated for 16 hours at 80° C. The reaction product was a clear fluid dispersion and included 0.4 millimolar (mmol) silane-substituted poly(ethylene oxide) oligomers per gram of 20-nm diameter silica nanoparticles.

A sample of 19.5 milligrams (mg) of fluorescein isothiocyanate (technical grade from Alfa Aesar, Ward Hill, Mass.) was added to a small vial. The dye was completely dissolved in 0.23 gram (g) of dry methyl sulfoxide (DMSO). A sample of 0.12 g of a 10% solution of 3-aminopropyltriethoxysilane in DMSO was added to the dye solution and reacted for 60 minutes at 60° C. to form a silane-functional fluorescein dye.

To an aqueous solution containing dispersed PEG-modified silica nanoparticles described above (58.5 g and 25 g of silica) was added the freshly prepared silane-functional fluorescein dye in DMSO. The mixture was subsequently heated for 16 hours at 60° C. to form fluorescein- and PEG-functional silica nanoparticles.

Examples 59-62

Nonspecific Binding of Fluorescent-Labeled Proteins to PEG-Functionalized Silica Nanoparticles For these examples, Phosphate Buffered Saline (PBS) consisted of 0.9% (w/v) NaCl in 10 mM sodium phosphate, pH=7.4. PBS/TWEEN consisted of PBS containing 0.05% (weight/volume) TWEEN 20 (Sigma). Fluorescein isothiocyanate (FITC) was obtained from Molecular Probes/Invitrogen (Carlsbad, Calif.). Nalco 2327 silica nanoparticles (20-nm silica particle) were obtained from Nalco Co. (Naperville, Ill.). PEG silane (poly(ethylene oxide) trimethoxy silane (PEG-silane), MW 500, available under the trade designation Silquest A-1230, was obtained from GE Silicones (Wilton, Conn.).

PEG-silane, Acrylate silane, and sulfonated silane modified nanoparticles were prepared by the following general procedure: Nalco 2327 silica nanoparticles (1 gram) at 40.0% solids in water was mixed with Silquest A-1230 PEG silane, sulfonated $((OH)_3Si(CH_2)_3OCH_2CH(OH)CH_2SO_3H)$ or carboxylated (carboxyethylsilanetriol) silane, and acrylate silane (3-acryloxypropyl trimethoxysilane, Gelest, Inc., Philadelphia, Pa.) in the amounts specified in Table 8. The amount of A-1230 PEG-silane was adjusted so the total silane charge (A-1230 PEG-silane+sulfonate silane+acrylate silane) was 0.65 mmol silane/gram of silica nanoparticles. The mixture of PEG-silane, sulfonated silane, and acrylate silane and silica nanoparticles was reacted for 4-6 hours at 80° C. in a sealed reaction vessel. After the reaction, the resulting reaction mixture was placed in a SPECTRA/POR 2 dialysis membrane (12-14,000 molecular weight cutoff molecular porous membrane tubing from Spectrum Laboratories, Inc. (Rancho Dominguez, Calif.). The membrane was placed in a vessel with continuous flowing deionized water for 20 hours.

TABLE 8

Mixtures for synthesis of modified silica nanoparticles.

| Example | Acrylate silane group | Shielding group | PEG-silane group | Weight % solids |
|---|---|---|---|---|
| 59 | 0.05 mmol | 0.6 mmol (sulfonated silane) | none | 8.51% |
| 60 | 0.05 mmol | 0.3 mmol (sulfonated silane)- | 0.3 mmol | 9.17% |
| 61 | 0.05 mmol | 0.6 mmol (carboxylated silane) | none | 8.97% |
| 62 | 0.05 mmol | 0.3 mmol (carboxylated silane) | 0.3 mmol | 9.34% |

To minimize the binding of proteins through the reactive acrylate groups, the acrylate groups were quenched with ethanolamine. To prepare the quenched particles, the silane-modified silica nanoparticles were suspended (at a concentration of $1 \times 10^{15}$ particles/ml) in 10 mM ethanol amine in sodium bicarbonate buffer, pH 9.0 for 2 hrs at room temperature. The particles were spun down at 13,000 rpm for 30 min.

The collected nanoparticles were then resuspended in 200 μl of PBS/TWEEN 20, and subsequently mixed with 100 μg/ml each of fluorescein isothiocyanate-labeled Cytochrome C and fluorescein isothiocyanate-labeled Bovine Serum Albumin (obtained by the reaction of FITC dye molecules with the protein mixture for 2 hours at room temperature, following the standard fluorescein labeling procedure from Molecular Probes/Invitrogen, Carlsbad, Calif.). The resulting mixture was then incubated for 1 hour at room temperature. After the incubation period, the particles were washed by centrifuging the suspension at 13,000 rpm, for 30 min, removing the supernatant, and resuspending the particles in 1 ml PBS/TWEEN 20. The wash step was repeated three times. 100 microliters of the thrice-washed, resuspended nanoparticle solution was placed into a microtiter plate and the amount of fluorescent protein bound to the particles was measured using a SpectraMax M2 Microplate fluorescence plate reader (Molecular Devices Corp., Sunnyvale, Calif.). The results, reported as relative light units (RLUs), are listed in Table 9.

TABLE 9

Binding of fluorescein-labeled protein to silica nanoparticles

| Sample | Shielding group | RLUs |
|---|---|---|
| Example 59 | Sulfonate | 440 |
| Example 60 | Sulfonate | 332 |
| Example 61 | Carboxylate | 533 |
| Example 62 | Carboxylate | 427 |
| Unmodified nanoparticles | None | 1087 |
| PBST buffer | None | 570 |

Example 63

Antibody Attachment to Acrylated Silica Nanoparticles and Bacteria Binding

*Staphylococcus aureus* strain 6538 was obtained from the American Type Culture Collection (ATCC, Manassas, Va.). Mouse monoclonal anti-*S. aureus* IgG antibody (Mab 107) is described in U.S. patent application Ser. No. 11/562,747, filed on Nov. 22, 2006, and entitled "ANTIBODY WITH PROTEIN A SELECTIVITY". Phosphate Buffered Saline (PBS) consisted of 0.9% (w/v) NaCl in 10 mM sodium phosphate, pH, 7.4. PBS/TWEEN consisted of PBS containing 0.05% (w/v) TWEEN 20 (Sigma). Fluorescein-conjugated Goat Anti-Mouse IgG (H+L) was obtained from Jackson Immunoresearch (West Grove, Pa.).

Acrylate silica nanoparticles, prepared as described in Examples 59-62, were suspended in PBS/Tween at a concentration of $10^{14}$ particles per milliliter. In this experiment, the percent solids for the particles from Examples 59-62 were 8.35%, 8.70%, 8.55%, and 8.17%, respectively. The particle suspensions were reacted with anti *S. Aureus* Mab 107 IgG antibody (75 μg/300 μL) for 2 hours at room temperature. The resulting particles were spun down at 13,000 revolutions per minute (rpm) for 30 minutes (min), and the particles were washed twice with PBS+0.05% TWEEN 20 to remove any non-conjugated antibody.

*S. aureus* ATCC 6538 (SA6358) was prepared by growing a culture overnight in TSB broth, washing the cells twice in PBS/TWEEN, and resuspending the cells in an equal volume of PBS/TWEEN 20. The cells were washed by centrifuging at 8000 rpm for 8 min at room temperature to pellet the cells, and resuspending the cells in PBS/TWEEN 20. The washed bacterial concentration was approximately $10^8$ cells/ml, which was estimated by an absorption measurement at 670 nm.

*S. aureus* 6538 bacteria at a concentration of $1 \times 10^8$ CFU/ml were allowed to incubate with the antibody-tethered silica particles for 30 min. The mixture was washed twice by centrifugation. Fluorescein-conjugated Goat Anti-Mouse IgG (H+L) (50 μg/ml) was introduced to the above incubation suspension containing the bacteria and antibody-tethered silica particles for labeling. This mixed solution was further incubated at room temperature for another 30 min. The samples were washed twice by centrifugation at 6000 rpm for 6 minutes each (Note: the relative centrifugal force of these wash steps was sufficient to pellet the bacterial cells but not the free acrylate nanoparticles). The pellet was resuspended and viewed through a Leica Fluorescence microscope. 100 μl aliquots of the solutions were placed into individual wells in a 96-well plate and were the relative fluorescence was measured using a SpectraMax M2 Microplate fluorescence plate reader (Molecular Devices Corp., Sunnyvale, Calif.). The excitation wavelength was 485 nm and the emission wavelength was 525 nm. No cut-off filter was used.

The negative control was an aliquot of the washed suspension of *S. aureus* cells. The positive control was an aliquot of the washed suspension of *S. aureus* cells, which had been incubated with the Mab 107 IgG antibody followed by incubation with the fluorescein-conjugated anti-mouse IgG antibody, as described above. The results are shown in Table 10.

Bright fluorescent labeling of bacteria was detected for the modified nanoparticles, which is representative of a relatively high level of binding of the antibody-conjugated nanoparticles to the bacteria. In contrast, very low or no fluorescence (relative to background) was detected for the negative control sample, where buffer was used instead of anti-*Staphylococcus aureus* antibody.

TABLE 10

Binding of antibody-conjugated nanoparticles, comprising water-dispersing groups and (optionally) PEG, to *S. aureus* cells. Results are presented in relative fluorescence units (RFU). In this experiment, an empty microplate well gave an average background reading of approximately 75 RFU. A microplate well containing PBS/Tween gave an average background reading of approximately 554 RFU.

| Sample | RFU |
| --- | --- |
| Nanoparticles (Example 59) with antibody | 828 |
| Nanoparticles (Example 59) control | 493 |
| Nanoparticles (Example 60) with antibody | 781 |
| Nanoparticles (Example 60) control | 543 |
| Nanoparticles (Example 61) with antibody | 862 |
| Nanoparticles (Example 61) control | 569 |
| Nanoparticles (Example 62) with antibody | 636 |
| Nanoparticles (Example 62) control | 591 |
| *S. aureus* Negative Control | 676 |
| *S. aureus* Positive Control | 744 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A solid support material having a surface, comprising:
   biomolecule-binding groups bonded to the surface through nonreversible covalent bonds;
   an aldehyde-containing biomolecule covalently bonded to one or more biomolecule-binding groups through an —Ar—N═C(H)— and/or —Ar—NHN═C(H)— linkage, wherein Ar is an aryl group; and
   shielding groups covalently bonded to the surface.

2. The composition of claim 1, wherein the aldehyde-containing biomolecule is a capture agent for a target biological analyte.

3. The solid support material of claim 1 wherein the shielding groups comprise poly(alkylene oxide)-containing groups.

4. The solid support material of claim 3 wherein the poly(alkylene oxide)-containing shielding groups comprise poly(ethylene oxide)-containing groups.

5. The solid support material of claim 1 comprising nanoparticles.

6. The solid support material of claim 5 further comprising water-dispersible groups covalently bonded to the surface, wherein the water-dispersible groups are distinct from the shielding groups.

7. The solid support material of claim 6 wherein the water-dispersible groups comprise carboxylic acid groups, sulfonic acid groups, phosphonic acid groups, salts thereof, or combinations thereof.

8. A method of preparing a solid support material having a biomolecule attached thereto, the method comprising:
   providing a solid support material comprising a surface;
   providing a shielding compound comprising a shielding group and a surface-bonding group;
   providing a biomolecule-binding compound comprising an alpha, beta-ethylenically or acetylenically unsaturated group, an electron withdrawing group, and a surface-bonding group;
   covalently bonding the shielding group and biomolecule-binding group to the surface of the solid support material through the surface-bonding groups; and
   contacting the solid support material with an amino-functional biomolecule under conditions effective to covalently bond the biomolecule to one or more biomolecule-binding groups through a carbon-nitrogen bond between the amino group of the biomolecule and the beta position of the alpha,beta-ethylenically unsaturated group.

9. The method of claim 8 wherein the biomolecule is a capture agent for a target biological analyte.

10. A method of preparing a solid support material having a biomolecule attached thereto, the method comprising:
    providing nanoparticles, each comprising a surface;
    providing a shielding compound comprising an organocarboxylate-containing and/or organosulfonate-containing group and a surface-bonding group;
    providing a biomolecule-binding compound comprising an acrylate group and a surface-bonding group;
    covalently bonding the organocarboxylate and/or organosulfonate group and acrylate group to the surface of the nanoparticles through the surface-bonding groups; and
    contacting the nanoparticles with an amino-functional biomolecule under conditions effective to covalently bond the biomolecule to one or more acrylate groups through a carbon-nitrogen bond between the amino group of the biomolecule and the beta position of the acrylate group.

11. The method of claim 9 wherein the biomolecule capture agent is an antibody.

12. The method of claim 8 wherein the biomolecule is a target biological analyte.

13. The method of claim 8 wherein the solid support material comprises particulate material.

14. The method of claim 13 wherein the particulate material comprises nanoparticles.

15. The method of claim 14 wherein the nanoparticles further comprise water-dispersible groups covalently bonded to their surfaces, wherein the water-dispersible groups are distinct from the shielding groups.

* * * * *

UNITED STATES PATENT AND TRADEMARK OFFICE
CERTIFICATE OF CORRECTION

PATENT NO. : 8,597,959 B2
APPLICATION NO. : 12/595862
DATED : December 3, 2013
INVENTOR(S) : Naiyong Jing It is certified that error appears in the above-identified patent and that said Letters Patent is hereby corrected as shown below:

Title Page,
Item (56), References Cited, under OTHER PUBLICATIONS, Column 1, Line 9, "Progess" should read --Progress--.
Item (56), References Cited, under OTHER PUBLICATIONS, Column 2, Line 31, "Therof" should read --Thereof--.

In the Specification,
Column 4,
Line 51, "nontertiarty" should read --nontertiary--.
Line 53, "nontertiarty" should read --nontertiary--.

Column 10,
Line 12, "oligmers" should read --oligomers--.

Column 13,
Line 40, "phosphato," should read --phosphate,--.

Column 17,
Line 3, "phosphato" should read --phosphate--.
Line 37, "interactions" should read --interactions.--.

Column 25,
Line 36, "acylamide-" should read --acrylamide- --.
Line 56, "acylamide-" should read --acrylamide- --.
Line 65, "-$CH_2$-β-" should read --$CH_2$-O- --.

Signed and Sealed this
Twenty-fourth Day of February, 2015

Michelle K. Lee
*Deputy Director of the United States Patent and Trademark Office*

CERTIFICATE OF CORRECTION (continued)
U.S. Pat. No. 8,597,959 B2

Column 35,
Line 15, "sheroplasts," should read --spheroplasts,--.
Line 22, "*Esherichia*" should read --*Escherichia*--.
Lines 34-35, "*stearothermophillus,*" should read --*stearothermophilus,*--.

Column 35,
Line 38, "*V. parahemolyticus,*" should read --*V. parahaemolyticus,*--.

Column 41,
Line 35, "milliters" should read --milliliters--.